United States Patent [19]

Kimura et al.

[11] Patent Number: 4,885,635
[45] Date of Patent: Dec. 5, 1989

[54] ENDOSCOPE LIGHT SOURCE APPARATUS

[75] Inventors: Kenji Kimura, Tachikawa; Hiroki Hibino, Hachioji; Toshiaka Nisikori, Sagamihara; Hisao Ogiu, Hachioji; Atsushi Kidawara, Tachikawa; Hisao Yabe; Koji Takamura, both of Hachioji; Jun Yoshinaga, Hino; Shinichi Kato, Oume; Takeaki Nakamura, Hino, all of Japan

[73] Assignee: Olympus Optical Co., Ltd., Tokyo, Japan

[21] Appl. No.: 346,299

[22] Filed: May 1, 1989

Related U.S. Application Data

[63] Continuation of Ser. No. 155,396, Feb. 12, 1988, abandoned.

[30] Foreign Application Priority Data

| Feb. 17, 1987 | [JP] | Japan | 62-34028 |
| Mar. 10, 1987 | [JP] | Japan | 62-54597 |
| Apr. 23, 1987 | [JP] | Japan | 62-100947 |

[51] Int. Cl.$^4$ .......................... H04N 7/18; H04N 9/04
[52] U.S. Cl. ....................................... 358/98; 358/42; 128/6
[58] Field of Search ................. 358/98, 42; 128/4, 6; 362/16, 18, 32, 293

[56] References Cited

U.S. PATENT DOCUMENTS

| 3,166,623 | 11/1965 | Waiclelich, Jr. | 358/98 |
| 4,625,236 | 11/1986 | Fuyimori et al. | 358/98 |
| 4,656,508 | 4/1987 | Yokata | 358/98 |
| 4,663,657 | 5/1987 | Nagasaki et al. | 358/98 |
| 4,729,018 | 3/1988 | Watanabe et al. | 358/98 |
| 4,740,837 | 4/1988 | Yanagisawa et al. | 358/98 |

FOREIGN PATENT DOCUMENTS

| 60-76888 | 5/1985 | Japan. |
| 60-243625 | 12/1985 | Japan. |
| 61-82731 | 4/1986 | Japan. |

Primary Examiner—John K. Peng
Attorney, Agent, or Firm—Armstrong, Nikaido, Marmelstein, Kubovcik & Murray

[57] ABSTRACT

This endoscope light source apparatus can feed illuminating lights to a scope provided with a frame sequential type imaging device, a scope provided with a color mosaic type imaging device and a fiber scope. This endoscope light source apparatus has a frame sequential light source part which can output a plurality of color lights and a white light source part which can output a white light. This frame sequential light source part has a filter which can output a plurality of color lights.

37 Claims, 29 Drawing Sheets (a)

(b)

ENDOSCOPE LIGHT SOURCE APPARATUS

This application is a continuation of application Ser. No. 155,396, filed Feb. 12, 1988, now abandoned.

FIELD OF THE INVENTION

This invention relates to an endoscope light source apparatus which can feed illuminating light to a scope provided with a frame sequential type imaging means, a scope provided with a color mosaic type imaging means and a fiber scope.

BACKGROUND OF THE INVENTION

Recently, there is extensively used an endoscope (called also a scope or fiber scope) whereby, by inserting an elongate insertable part through a body cavity, organs within the body cavity can be observed or, as required, by using a treating tool inserted through a treating tool channel, various curving treatments can be made.

Also, there are suggested various electronic scopes wherein a solid state imaging device such as a charge coupled device (CCD) is used. There are advantages that such an electronic scope is higher in the resolution and easier to record and reproduce picture images than the fiber scope and it is easier in such a picture image process to magnify of the picture image and to compare two picture images.

As systems of imaging color picture images of the above mentioned electronic scope, there are a frame sequential type sequentially switching the illuminating light to R (red), G (green) and B (blue) as shown, for example, in the gazette of a Japanese patent laid open No. 82731/1986 and a color mosaic type (called also a synchronous type) in which a filter array in which color filters respectively transmitting color lights of R, G and B are arranged in a mosaic form is provided on the front surface of a solid state imaging device. The frame sequential type has an advantage because the number of pixels can be made smaller than in the color mosaic type. On the other hand, the color mosaic type has an advantage because no color is displaced.

The above mentioned electronic scope can be varied depending upon the objects on which it is used. For example, for the upper or lower digestive organ, an insertable part of an outside diameter of about 10 mm is used. On the other hand, for the bronchus, usually an outside diameter less than about 5 mm is required. It is unreasonable physically and functionally to use the same kind of imaging device and the same kind of imaging system for various electronic scopes of outside diameters of the insertable parts in such a wide range. That is to say, in order to realize an electronic scope, for example, for the bronchus (fine diameter), an imaging device of a small number of pixels must be used.

In case the number of pixels is small, in order to prevent the reduction of the resolution, the frame sequential type color imaging system, wherein an object is illuminated in a frame sequential system with the lights of the respective wavelengths of R, G and B and is frame sequentially imaged under the illumination and the images are composed and color-displayed, is more advantageous than the color-mosaic type imaging system using color mosaic filters.

On the other hand, it is advantageous for the improvement of the picture quality to make the imaging system a color mosaic type by making the number of pixels large for the outside diameter of about 10 mm.

Now, the above mentioned fiber scope or electronic scope is used as connected to a light source apparatus generally feeding illuminating lights adapted to the respective scopes.

The illuminating method is different in the above mentioned fiber scope, frame sequential type electronic scope and color mosaic type electronic scope. That is to say, the fiber scope and color mosaic type electronic scope require a white light and the frame sequential type electronic scope requires a light sequentially switchable to R, G and B. However, the conventional light source apparatus can output only an illuminating light corresponding to either of the frame sequential type electronic scope and color mosaic type electronic or fiber scope. Therefore, the user is required to prepare respectively different light source apparatus depending on the kind of the scope and the economy and efficiency were low. In the gazette of a Japanese patent laid open No. 243625/1985, there is disclosed a connecting system whereby a fiber scope provided with an image transmitting optical fiber bundle is connected to a control apparatus of an electronic scope provided with a frame sequential type light source apparatus so that the object image may be observed on the displaying picture surface of a monitor television or the like. However, in this system, the color mosaic type electronic scope can not be used and the image cannot be observed with a naked eye by using the fiber scope.

OBJECTS AND SUMMARY OF THE INVENTION

An object of the present invention is to provide an endoscope light source apparatus which can feed illuminating lights to a scope provided with a frame sequential type imaging, a scope provided with a color mosaic type imaging and a fiber scope whereby a naked eye observation is possible.

The endoscope light source apparatus according to the present invention can connect a scope provided with a frame sequential type imaging, a scope provided with a color mosaic type imaging and a fiber scope whereby a naked eye observation is possible. This endoscope light source apparatus is provided with a frame sequential light outputting which can sequentially repeatedly radiate a plurality of color lights onto an object to be imaged and a white light outputting which can radiate a white light onto the object.

The other features and advantages of the present invention will become apparent enough with the following explanation.

BRIEF DESCRIPTION OF THE DRAWINGS

FIG. 1 is a perspective view showing the entire system of an endoscope apparatus.

FIG. 2 is a block diagram showing the formation of the endoscope apparatus.

FIG. 3 is an explanatory view showing the formation of a fiber scope fitted with a frame sequential type externally fitted camera.

FIG. 4 is an explanatory view showing the formation of a fiber scope fitted with a mosaic type externally fitted camera.

FIG. 5 is an explanatory view showing the formation of a fiber scope.

FIG. 6 is a block diagram showing the formation of a frame sequential type process circuit. FIG. 7 is a block diagram showing the formation of a mosaic type process circuit.

FIG. 9 is a block diagram showing the formation of a control apparatus.

FIG. 10 is a block diagram showing the formation of an output circuit.

FIG. 11 is a perspective view showing connectors and connector receptacles.

FIG. 12 is a block diagram showing the formation of a control apparatus.

FIG. 13 is an explanatory view showing another state of FIG. 12.

FIG. 14 is a perspective view showing connectors and connector receptacles.

FIG. 21 is a block diagram showing the formation of a control apparatus.

FIG. 22 is an explanatory view showing another state of FIG. 21.

FIG. 23 is a block diagram showing the formation of a control apparatus.

FIG. 24 is an explanatory view showing a rotary filter.

FIG. 25 is a block diagram showing a frame sequential process circuit.

FIG. 26 is a perspective view showing the appearance of an endoscope apparatus.

FIG. 27 is a block diagram showing a frame sequential type scope as combined.

FIG. 28 is a block diagram showing a mosaic type scope as combined.

FIG. 30 is a perspective view showing a rotary filter.

FIG. 31 is an explanatory view showing another state of FIG. 30.

FIGS. 33 t 35 relate to the eighth embodiment of the present invention.

FIG. 37 is a magnified view of a connector of a frame sequential type electronic scope.

DETAILED DESCRIPTION OF PREFERRED EMBODIMENTS

Embodiments of the present invention shall be explained with reference to the drawings in the following.

FIGS. 1 to 7 show the first embodiment of the present invention.

Figure 1:
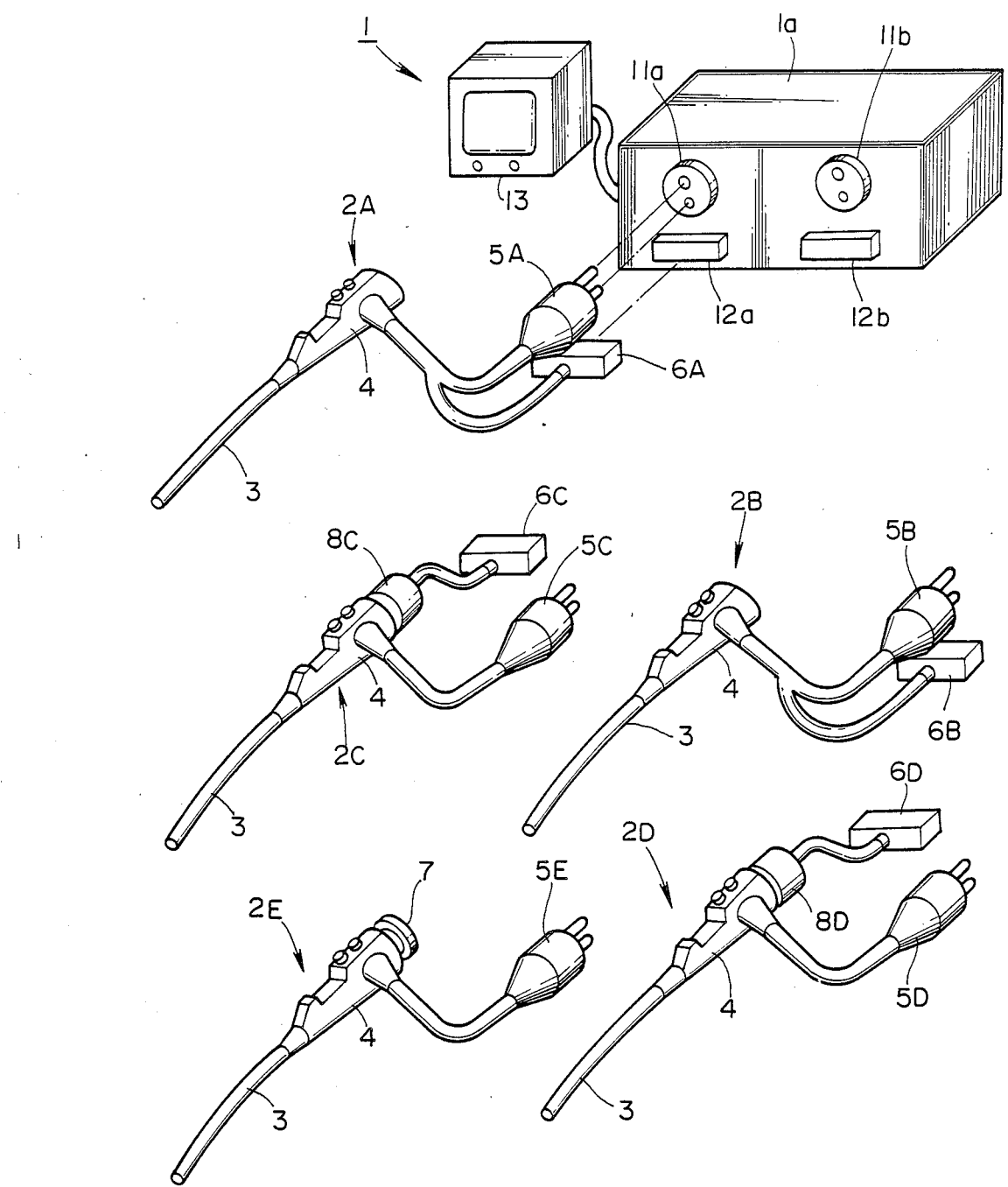
FIGS. 1 to 7 relate to the first embodiment of the present invention.

As shown in FIG. 1, an endoscope apparatus 1 is provided with a control apparatus 1a in which a light source apparatus of this embodiment and a video processor processing video signals are contained and to which any of various scopes (endoscopes) 2A, 2B, 2C, 2D and 2E can be connected. As scopes, there are five kinds as shown in the drawing, that is, a frame sequential type electronic scope 2A, a color mosaic type electronic scope using a color mosaic filter 2B, a fiber scope externally fitted with a frame sequential type television camera (which shall be mentioned hereinafter as a fiber scope fitted with a frame sequential type television camera) 2C, a fiber scope externally fitted with a color mosaic type television camera (which shall be mentioned hereinafter as a fiber scope fitted with a color mosaic type television camera) 2D and a fiber scope 2E.

Each of the above mentioned scopes 2A, 2B, 2C, 2D and 2E has an elongate insertable part 3 and an operating part 4 connected to the rear end side of this insertable part 3. A universal cord 5 is extended from this operating part 4 and is provided at the tip with a light source connector 5A, 5B, 5C, 5D or 5E. In each of the frame sequential type electronic scope 2A and color mosaic type electronic scope 2B, the above mentioned universal cord 5 is provided on the tip side with not only a light source connector 5A or 5B but also a signal connector 6A or 6B. In the fiber scope 2C fitted with the frame sequential type television camera and the fiber scope 2D fitted with the color mosaic type television camera, a frame sequential television camera 8C and a color mosaic type television camera 8D are respectively fitted to the eyepiece part 7 of the fiber scope 2E and the signal cables extended respectively from the television cameras 8C and 8D are provided at the tip respectively with signal connectors 6C and 6D. Two sets of connector receptacles are provided, for example, on the front surface of a housing of a control apparatus 1a so that the connectors 5A, 6A; 5B, 6B; 5C, 6C; 5D, 6D; 5E respectively of above mentioned respective scopes 2A, 2B, 2C, 2D and 2E (hereinafter, in case all of scopes these are common with each other, they are represented by the reference numeral 2) may be connected to set the respective scopes 2 in a usable state. These connector receptacles consist of a frame sequential type light source connector receptacle 11a and frame sequential signal connector receptacle 12a and a white light source connector receptacle 11b and color mosaic type signal connector receptacle 12b. The above mentioned frame sequential type light source connector 11a is in the form to which the light source connectors 5A and 5C of the same shape with each other of the frame sequential type electronic scope 2A and the fiber scope 2C fitted with the frame sequential type television camera (these two scopes 2A and 2C are mentioned also as frame sequential type scopes) can be respectively connected. The frame sequential type signal connector receptacle 12a adjacent to the lower side of the above mentioned frame sequential type light source connector receptacle 11a is in the form to which the respective signal connectors 6A and 6C of the same shape with each other of the frame sequential type electronic scope 2A and the fiber scope 2C fitted with the frame sequential type television camera, that is, the frame sequential type scopes 2A and 2C can be connected.

On the other hand, so that the light source connector 5B of the color mosaic type electronic scope 2B, the light source connector 5D of the fiber scope 2D fitted with the color mosaic type television camera (these two scopes 2B and 2D are mentioned also as mosaic type scopes) and the light source connector 5E of the fiber scope 2E may be respectively connected to the white light source connector receptacle 11b, these connectors 5B, 5D and 5E are of the same shape. Also, so that the signal connector 6B of the color mosaic type electronic scope 2B and the signal connector 6D of the fiber scope 2D fitted with the color mosaic type television camera may be connected to the color mosaic type signal connector receptacle 12b adjacent to the lower side of this white light source connector receptacle 11b, these connectors 6B and 6D are of the same shape.

In case the above mentioned fiber scope 2E is used as connected, the object is observed with a naked eye but in case the other scopes 2A, 2B, 2C and 2D are used, the imaged object can be color-displayed by a color monitor 13 connected to the signal output end of the control apparatus 1a.

In this embodiment, each of the light source connectors 5A, 5B, 5C, 5D and 5E in the respective scopes 2 is provided with a light guide connector and air and water feeding connector and the connector receptacles 11a and 11b can connect them.

The interiors of the above mentioned respective scopes 2A, 2B, 2C, and 2D and 2E are formed as shown respectively in FIGS. 2 to 5.

In each scope 2, a light guide 14 transmitting an illuminating light is inserted, the illuminating light fed to the entrance end surface from a light source part 15a or light source part 15b of a light source apparatus 15 within the control apparatus 15 within the control apparatus 1a is transmitted to the exit end surface side and can illuminate the object side in front through a light distributing lens 16 arranged in front of this exit end surface.

In each above mentioned scope 2, an image forming objective 17 is arranged in the tip part of the insertable part 3. In the image forming position of this objective 17, in the frame sequential type or color mosaic type electronic scope 2A or 2B, a solid state imaging device 18 such as a CCD is arranged, on the other hand, in the fiber scope 2E and fiber scope 2C or 2D fitted with the television camera 8C or 8D, the entrance end surface of the image guide 19 is arranged to be present.

An eyepiece 21 is arranged as opposed to the exit end surface of the image guide 19. In the fiber scope 2E, the object can be observed with a naked eye brought close to the eyepiece 7.

On the other hand, where the frame sequential type television camera 8C or color mosaic type television camera 8D is fitted to the eyepiece part 7 of the fiber scope 2E, a solid state imaging device 22 is arranged through an image forming lens, not illustrated as opposed to the eyepiece 21.

The optical image formed on the imaging surface of a solid state imaging device 18 or 22 forming an imaging means is photoelectrically converted, is amplified by a preamplifier 24, is then transmitted to the signal connector 6 (representing 6A, 6B, 6C and 6D) side and is input into a video processor 25a or 25b through the signal connector receptacle 12a or 12b to which this connector 6 is connected. A solid state imaging device driving clock is applied to each solid state imaging device 18 or 22 from the driver 26a or 26b of the above mentioned video processor 25a or 25b.

The other scopes than the fiber scope 2E are provided with type signal generating circuits 27A, 27B, 27C and 27D outputting scope discriminating type signals so that the type may be discriminated by a discriminating circuit 28a or 28b within the control apparatus 1a through, the signal connector 6.

Figure 2:
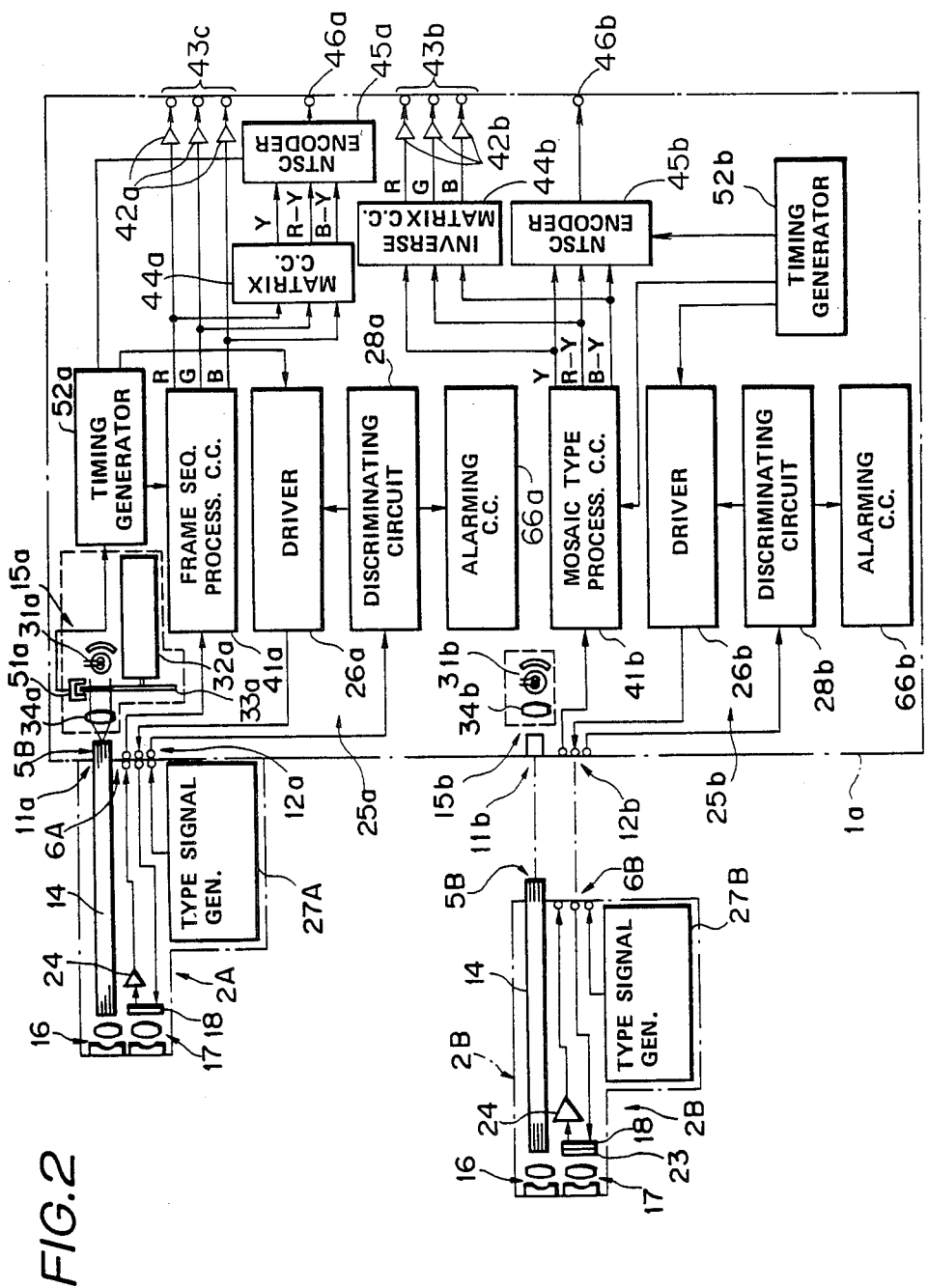
Figure 3:
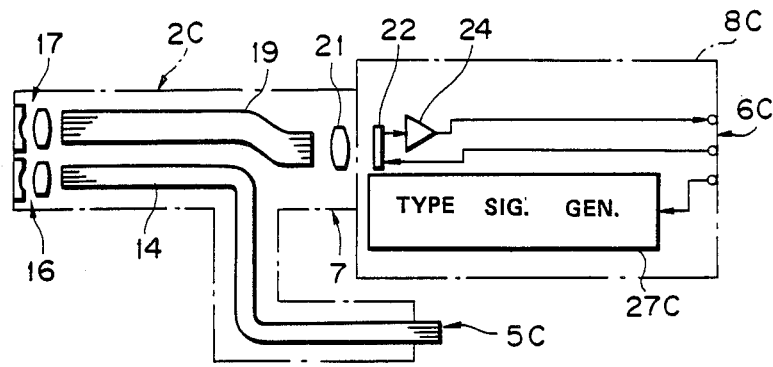
Figure 4:
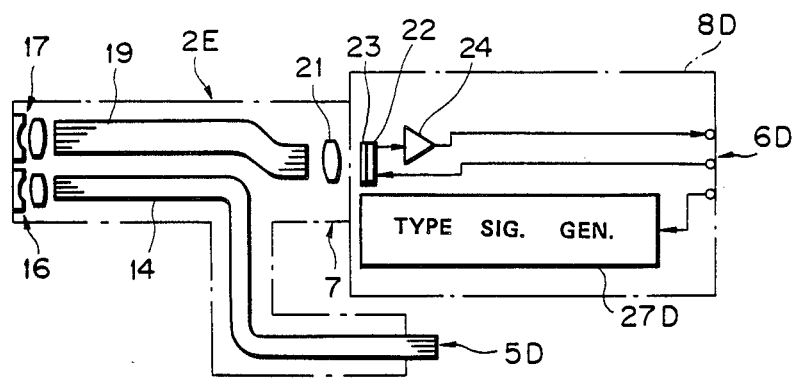
Figure 5:
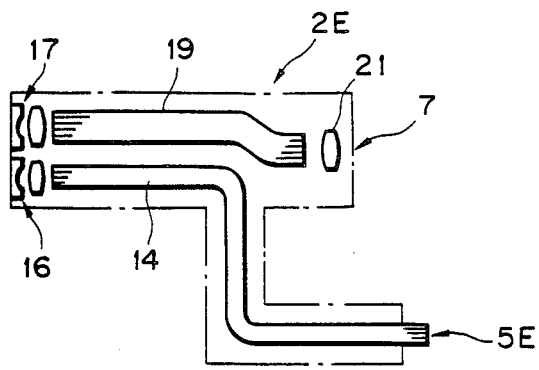

Now, within the control apparatus 1a to which any of the above mentioned scopes 2 is connectable, as shown in FIG. 2, a light source apparatus 15 consisting of two sets of light source parts 15a and 15b and two sets of video processors 25a and 25b are contained.

One light source part 15a is of a frame sequential type and is provided with a light source lamp 31a emitting a white light and a rotary filter 33 having three primary color transmitting filters of (red (R), green (G) and blue (B) and rotated and driven by a motor 32a. The white light emitted from the above mentioned light source lamp 31a is sequentially made illuminating lights of the respective wave lengths of R, G and B through the above mentioned rotary filter 33, is condensed by a condenser lens 34a and is fed to the entrance end surface of the light guide 14 fitted to the connector receptacle 11a.

The other light source part 15b is a white light source and is provided with a white light source lamp 31b emitting a white light. The white light emitted from this white light source lamp 31b is condensed by a condenser lens 34b and is fed to the entrance end surface of the light guide 14 fitted to the connector receptacle 11b.

Now, one video processor 25a is for frame sequential signal processing and the signal input into the signal inputting terminal of the frame sequential type signal connector receptacle 12a is input into a frame sequential type process circuit 41a and the signals imaged respectively under the illuminating lights of the respective wavelengths of R, G and B are output as color signals R, G and B. These respective color signals R, G and B are output as three primary color signals R, G and B from three primary color output ends 43 through drivers formed respectively of buffers 42a. The above mentioned color signals R, G and B are transmitted through a matrix circuit 44a to produce luminance signal Y and color difference signals R−Y and B−Y which are then input into an NTSC encoder 45a, are converted to an NTSC system composite video signal which is output from the NTSC output end 46a.

A rotary position sensor 51a detecting the rotary position is provided in one place on the outer periphery of the rotary color filter 33a of the above mentioned frame sequential type light source part 15a. By the output of this rotary position sensor 51a, the timing of the clock of the timing generator 52a is synchronized with the rotation of the rotary filter 33a and the output of this timing filter 33a and the output of this timing generator 52a controls the timing of the frame sequential type process circuit 41a.

Figure 6:
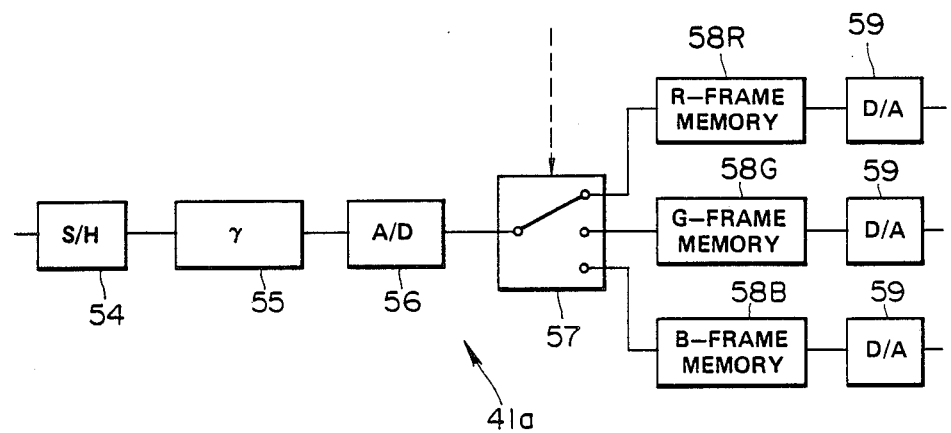

The above mentioned frame sequential type process circuit 41a is formed as shown, for example, in FIG. 6.

That is to say, the signal input through the preamplifier is input into a sample holding circuit 54, is sample held, is γ-corrected by a γ-correcting circuit 55 and is converted to a digital signal by an A/D converter 56. The signals imaged under the frame sequential illuminations of R, G and B through a multiplexer 57 switched by the signal of the above mentioned timing generator 52a are written into an R frame memory 58R, G frame memory 58G and B frame memory 58B. The signal data written into these respective frame memories 58R, 58G and 58B are simultaneously read out, are respectively converted to analogue color signals R, G and B by a D/A converter 59 and are output to the above described matrix circuit 44a side.

On the other hand, the signal imaged by the solid state imaging device 18 or 22 through the color mosaic type signal connector 12b is input into the color mosaic type process circuit 41b and a luminance signal Y and color difference signals R−Y and B−Y are output, are input into an NTSC encoder 45b and are converted to a composite video signal of an NTSC system which is output from the NTSC output end 46b. Also, they are input into an inverse matrix circuit 44b and are converted to color signals R, G and B. The three primary color signals R, G and B are output from the three primary color output ends 43b respectively through buffers 42b forming drivers.

Figure 7:
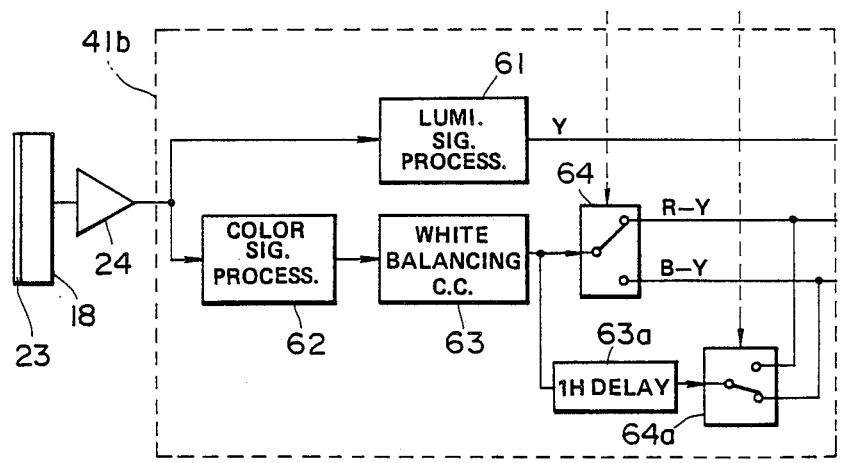

The above mentioned color mosaic type process circuit 41b is formed as shown, for example, in FIG. 7.

That is to say, the signal from the solid state imaging device 18 or 22 as amplified by the pre-amplifier 24 is transmitted through the luminance signal processing circuit 61 to produce a luminance signal Y. It is also input into a color signal reproducing circuit 62, color difference signals R−Y and B−Y are produced on each horizontal line in time series and are white balance compensated in a white balance circuit 63. One is input directly into an analogue switch 64. The other is delayed by 1 horizontal line in a 1H delay line 63a and is input into the analogue switch 64a and, by the switching signal of a timing generator 52b, a color difference signals R−Y and B−Y are obtained.

The respective timing generators 52a and 52b apply signals respectively to the drivers 26a and 26b and NTSC encoders 45a and 45b and control to process signals synchronized with driving pulses used to read signals out of the solid state imaging device 18 or 22. In this case, in the frame sequential video processor 25a, the above mentioned timing generator 52a is synchronized with the rotary color filter 33 by the output of the position sensor 51a. The above mentioned NTSC encoders 45a and 45b are formed to contain buffers.

Now, the type signal generating circuits 27A, 27B, 27C and 27D are formed by connecting resistances of respectively different resistance values, for example, between two terminals. On the other hand, the discriminating circuits 28a and 28b can discriminate the connected scope of any resistance value by using a comparator or the like of the resistance value between two terminals.

In case the signal connector 6B or 6D of the color mosaic type electronic scope 2B or the fiber scope 8D fitted with the color mosaic type television camera is connected, for example, to the frame sequential type signal connector receptacle 12a, it is discriminated by the discriminating circuit 28a that the resistance value is not for the frame sequential type and, by the discriminated signal, the user is informed of the warning sound by the warning circuit 66 or of the flickering by an LED.

Also, in case the connector 6A of the frame sequential type electronic scope 2A or the connector 6C of the fiber scope 2C fitted with the frame sequential type television camera is connected to the color mosaic type signal connector receptacle 12b, it will be discriminated by the discriminating circuit 28b and will be warned by the warning circuit 66b.

On the other hand, when the connector 6A or 6C of the frame sequential type scope 2A or 2C is connected to the frame sequential type signal connector receptacle 12a, the warning circuit 66a will not operate and will not be warned. (When the connection is right, it may be indicated by lighting the LED.) Likewise, when the connector 6B or 6D of the color mosaic type scope 2B or 2D is connected to the color mosaic type connector receptacle 12b, the warning circuit 66b will not operate. (The right connection may be discriminated and may be indicated by the lighting of the LED of a position or color different from the case of warning.) Also, the case that two signal connectors are simultaneously connected to both signal receptacles 12a and 12b may be warned. A light source connector connection sensing means is provided inside the frame sequential type light source connector receptacle 11a so that, in case the connector 5e of the fiber scope 2e is connected, the mis-connection may be made known. That is to say, in case the connector 5E is connected to the connector receptacle 11a and no connector is connected to the signal connector receptacles 12a and 12b, it will be warned.

Thus, in this embodiment, the light source apparatus 15 contained within the control apparatus 19 has a frame sequential type light source part 15a and white light part 15b. The above mentioned frame sequential type light source part 15a feeds an illuminating light to the light guide 14 of the frame sequential type electronic scope 2A or the fiber scope 2C fitted with the frame sequential type television camera connected to the frame sequential type light source connector receptacle 11a. On the other hand, the above mentioned white light source part 15b feeds an illuminating light to the light guide 14 of the color mosaic type electronic scope 2B, fiber scope 2D fitted with the color mosaic type television camera or fiber scope 2E connected to the white light source connector receptacle 11b.

Therefore, even if any of the frame sequential type scopes 2A and 2C, color mosaic type scopes 2B and 2D and fiber scope 2E is connected, the illuminating light corresponding to the connected scope can be fed.

Also, the above mentioned control apparatus 19 is provided with not only the above mentioned light source apparatus 15 but also the frame sequential type video processor 25a and color mosaic type video processor 25b.

Therefore, the signal process corresponding to the frame sequential type scopes 2A and 2C or the color mosaic type scope 2B and 2D can be made and the object images imaged by the respective scopes can be color-displayed in the color monitor 13.

In the case of using the fiber scope 2E, by connecting its light source connector 5E to the white light source connector receptacle 11b, a white light can be fed to this fiber scope 2E and the object can be observed with a naked eye.

Further, in this embodiment, in case a wrong scope is connected to the two sets of connector receptacles 12a and 12b provided in the control apparatus 1a, it will be sensed by the discriminating circuit 28a or 28b that the connection is not right and will be warned by a warning circuit 66a or 66b.

Therefore, when one unit of the control apparatus 1a is provided, scopes different in the color imaging system can be accommodated and even the fiber scope 2E can be simultaneously used. In the case of a wrong connection, it will be warned. Therefore, the apparatus is convenient to use. If the connector 6 (connector receptacle 12) is made different in the shape between the frame sequential type and mosaic type, the mis-connection can be eliminated.

The signals after the signal process for above mentioned two color imaging systems are the same in the output type. That is to say, as they are the same as the three primary color outputs or the video signals of the NTSC system, the same color monitor 13 can be used. (This color monitor may correspond to the three primary colors or may have video signal of the NTSC system input.)

In case the television camera 8C or 8D is fitted to the fiber scope 2E, the imaged picture image will be displayed in the color monitor 13 but, in case the television camera 8C or 8D is removed, the removed state may be displayed on the picture surface of the color monitor 13. That is to say, for example, it may be displayed that the observation is being made by the fiber scope 2E or a fixed picture image may be displayed.

Figure 8:
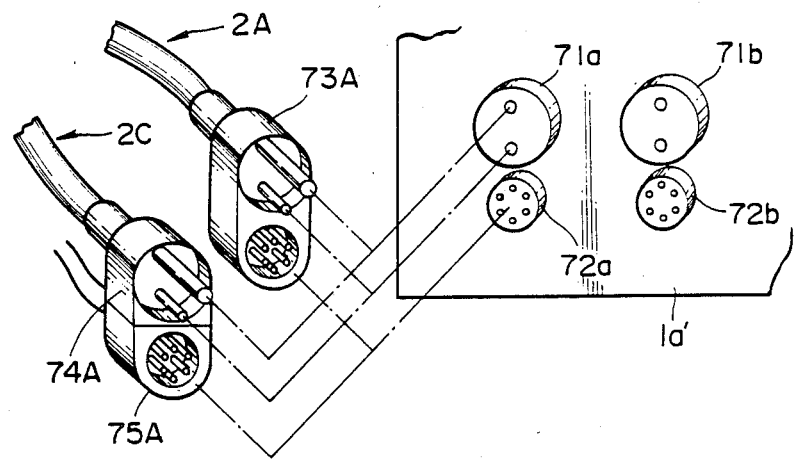
FIG. 8 is a perspective view showing modifications of connectors and connector receptacles.
Figure 8:
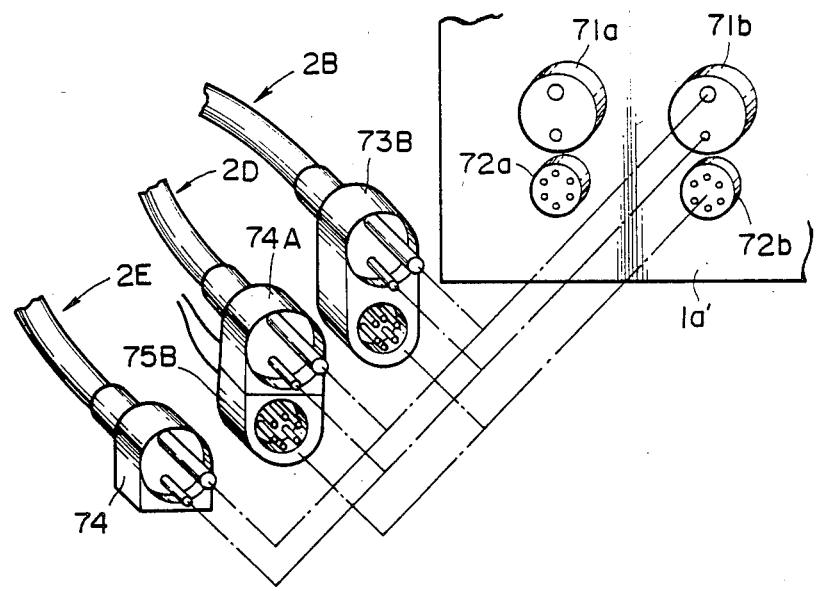

FIG. 8 shows modifications of the connectors and connector receptacles.

An imaging apparatus body 1a' is provided with a round frame sequential light source connector receptacle 71a and signal connector receptacle 72a; and a white light source connector receptacle 71b and color mosaic type signal connector receptacle 72b as separated on the housing front surface or the like. Both connector receptacles 71a and 71b or 72a and 72b are of the same shape.

On the other hand, as shown in FIG. 8(a), the frame sequential type scope 2A is provided with a connector 73A integrating the light source connector part and signal connector part so as to be connectable to the frame sequential light source connector receptacle 71a and signal connector receptacle 72a.

Likewise, as shown in FIG. 8(b), the color mosaic type scope 2B is provided with a connector 73B connectable to the above mentioned white light source connector receptacle 71b and color mosaic type signal connector receptacle 72b.

Also, as shown in FIG. 8(a), when the light source connector 74A and signal connector 75A are combined, the fiber scope 2C fitted with the frame sequential type television camera can be made in the same form as of the connector 73A of the above mentioned frame sequential type electronic scope 2A and can be used as connected to the frame sequential type connector receptacles 71a and 72a. Also, as shown in FIG. 8(b), when the light source connector 74A and signal connector 75B are combined, the fiber scope 2D fitted with the color mosaic type television camera can be made in the same form as of the connector 73B of the above mentioned color mosaic type electronic scope 2B and can be connected to the white light source connector receptacle 71b and signal connector receptacle 72b.

By connecting the light source connector 74 of the fiber scope 2E to the white light source connector receptacle 72b, a white light can be fed toward the light guide and a naked eye observation can be made.

If a connection different from the connection shown in FIG. 8(a) and (b) is made, as explained in the first embodiment, by connecting the signal connector, the signal of the type signal generating circuit is discriminated by the discriminating circuit and a warning is issued.

Figure 9:
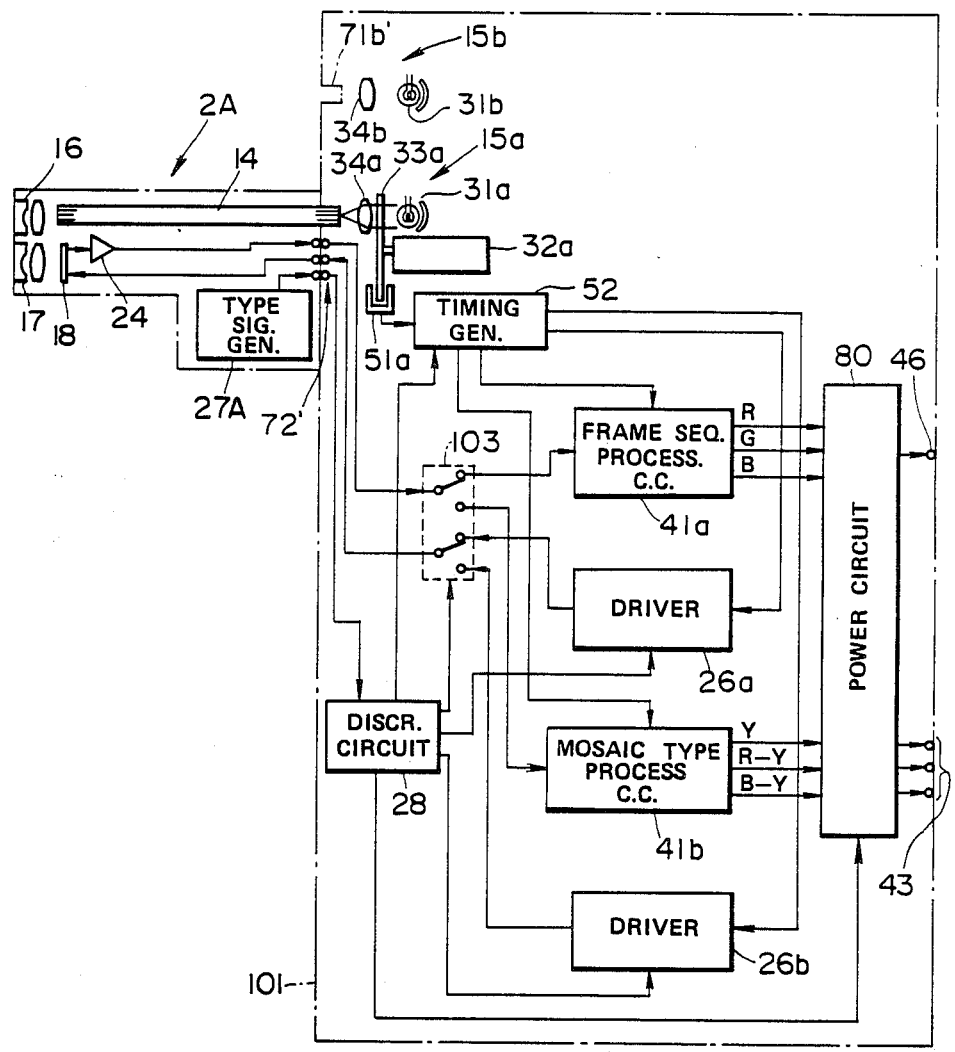
FIGS. 9 to 11 relate to a modification of the first embodiment.
Figure 10:
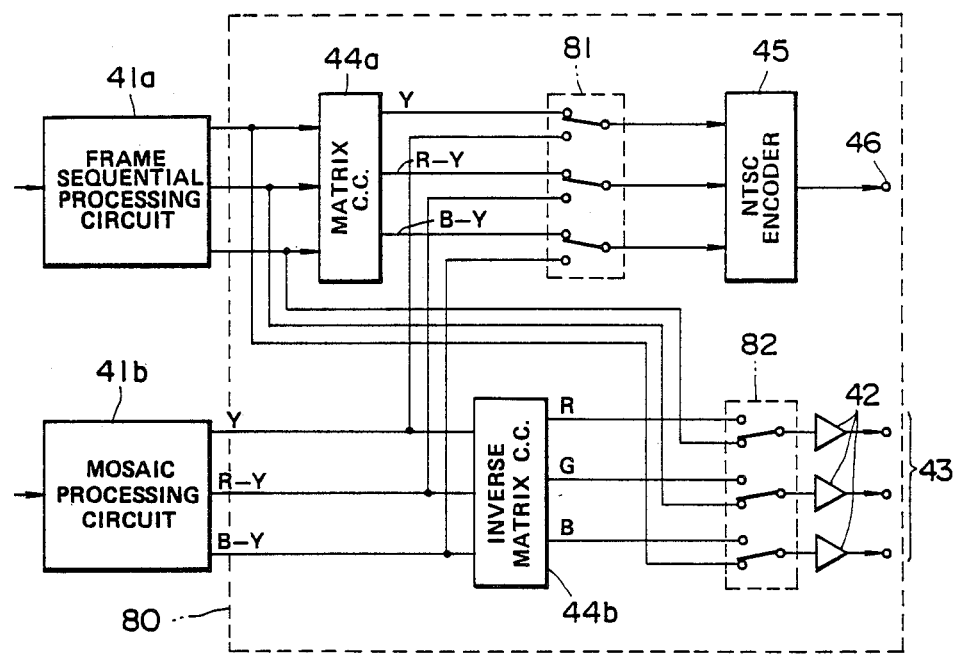
Figure 11:
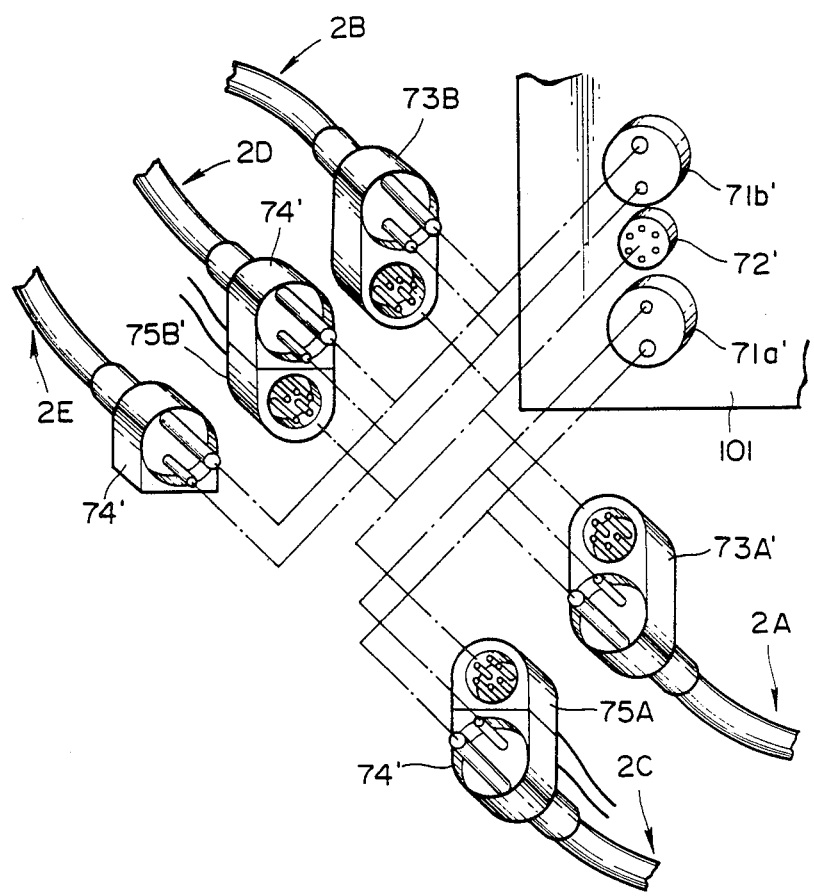

FIGS. 9 to 11 show a modification of the first embodiment.

In this modification, as shown in FIG. 9, in a control apparatus 101, the signal input end of the electronic scope 2 is made common and the output side is also made common.

A signal connector receptacle 72' common with light source connector receptacles 71a' and 71b' of this control apparatus is in the form shown, for example, in FIG. 11, a connector 73A' of the frame sequential type scope 2A and a connector 73B' of the mosaic type electronic scope 2B can be connected in the respective signal connector parts to a common signal connector receptacle 72' and in the light source side connector parts to light source connector receptacles 71a' and 71b' provided respectively above and below. Likewise, a light source connector 74' and signal connector 71A' of the scope 2C fitted with the frame sequential type television camera or connectors 74' and 75B' of the scope 2D fitted with the mosaic type television camera are made the same. Further, a connector 74' of the fiber scope 2E can be connected to the white light source connector receptacle 71'. The internal formation of the above mentioned control apparatus 101 is as shown in FIG. 9.

As shown in FIG. 9, for example, the output signal of the type signal generating circuit (for example, 27A) input into the common discriminating circuit 28 through the common signal connector receptacle 72' discriminates the connected scope in the discriminating circuit 28. This discriminating circuit 28 controls not only both drivers 26a and 26b as in the first embodiment but also the switching of the newly provided switching 103. For example, as shown in FIG. 9, when the frame sequential type scope 2A or 2C is connected, the switching switch will be switched to the field sequential side, the driving pulse of the driver 26a will be applied to the solid state imaging device 18 through the connector and the signal read out of the solid state imaging device 18 will be input into the frame sequential type process circuit 41a.

On the other hand, when the frame sequential type scopes 2A and 2C are not connected, the mosaic type process circuit side will be selected. By detecting the case of the mosaic type scope 2B or 2C, the switching switch 103 may be switched to the mosaic type side.

The above mentioned discriminating circuit 28 feeds a control signal also to a timing generator 52 made common and can accommodate either system.

In this modification, the signal transmitted through the process circuit 41a or 41b is output through an output circuit 80 shown, for example, in FIG. 10.

This output circuit 80 is provided with a 3-circuit 2-contact switching switch 81 between the output end of the matrix circuit 44a and the NTSC encoder 45a and also with a 3-circuit 2-contact switching switch 82 between the output end of the inverse matrix circuit 44b and the buffers 41 forming the driver.

When the above mentioned switching switch 81 is ON on one contact side, the signal of the matrix circuit 44a will be led to the common NTSC encoder 45, will be made a video signal of the NTSC system in this NTSC encoder 45 and will be output from a common NTSC output end 46. When the other contact side is selected, the signal of the mosaic type process circuit 41b will be led to the NTSC encoder 45 end will be output from the common NTSC output end 46.

On the other hand, on the other switching switch 82, when the frame sequential side is selected, the output signal of the frame sequential type process circuit 41a will be transmitted through the common buffers 42 forming the driver and three primary color signals will be output from the common RGB output ed 42. When the mosaic type process circuit side is selected, three primary color signals R, G and B transmitted through the inverse matrix circuit 44b will be output from the RGB output end 43.

The above mentioned switching switches 81 and 82 can be respectively manually switched or can be switched as operatively connected. Also, as shown in FIG. 2, the type signal output from the connected scope is discriminated by the discriminating circuit 28 and, by this discriminating circuit 28, the above mentioned both switching switches 81 and 82 can be switched to a process circuit 41a or 41b processing signals corresponding to the connected scope.

Without using the output circuit 80 shown in the above mentioned FIG. 10, as shown in FIG. 2, the output end may be separate for the frame sequential type and mosaic type.

Two light source lamps 31a and 31b may be provided on both sides passing through the center of the rotary plate so as to be able to be exchanged and used as auxiliary lights by the rotating operation.

In this modification, if the light source connector of the fiber scope 2E is connected to the imaging apparatus body 101, a naked eye observation can be made as in the first embodiment.

In case only the connector 74' of the fiber scope 2E is connected to the white light source connector receptacle 71b', by providing the connection sensing means, it may be displayed by the monitor that the fiber scope 2E is connected.

Figure 12:
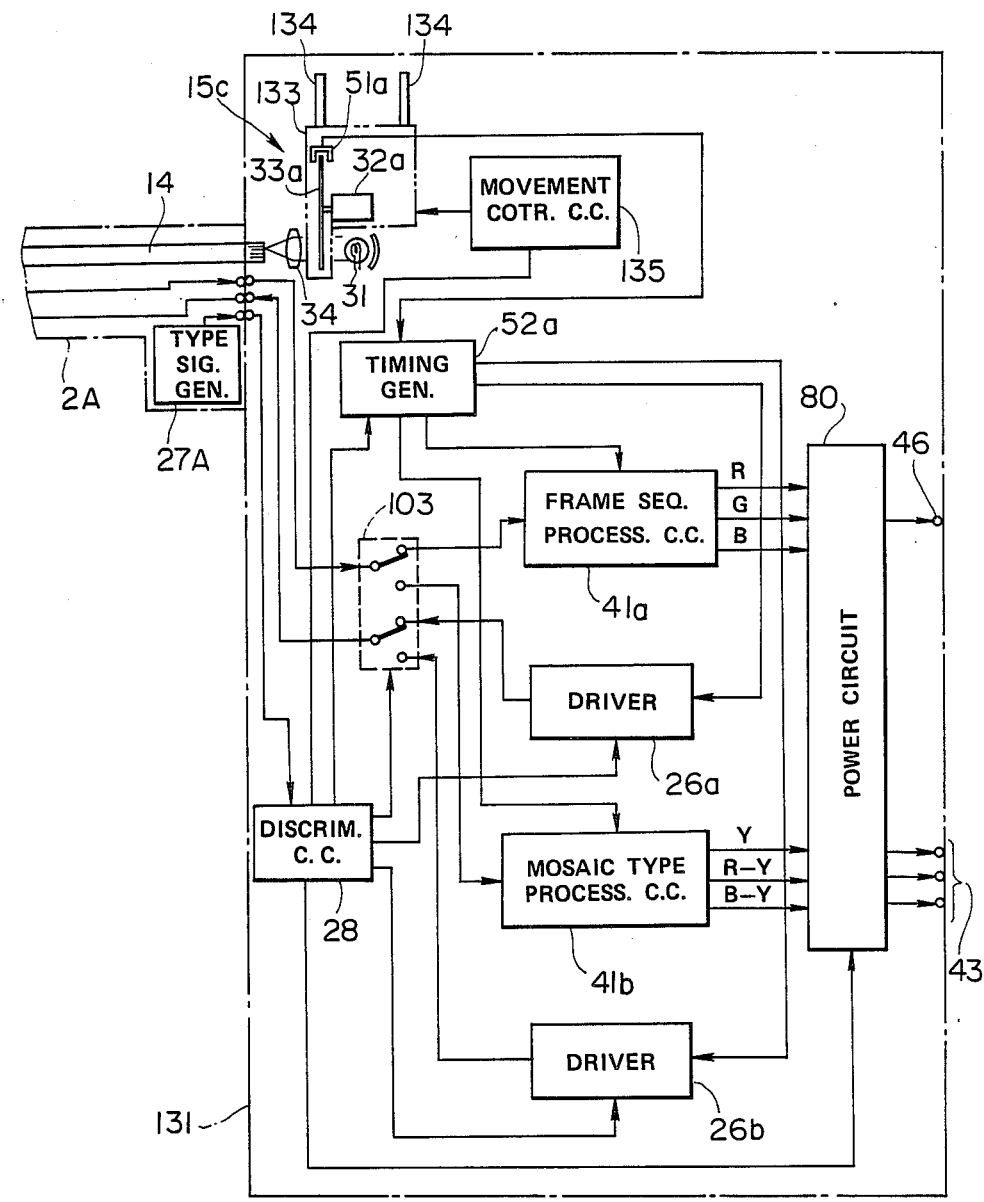
FIGS. 12 to 14 relate to the second embodiment of the present invention.
Figure 13:
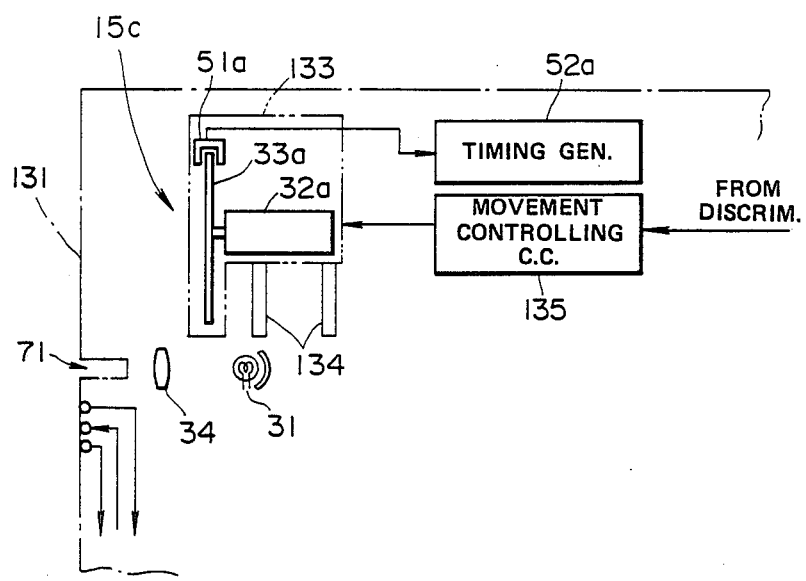
Figure 14:
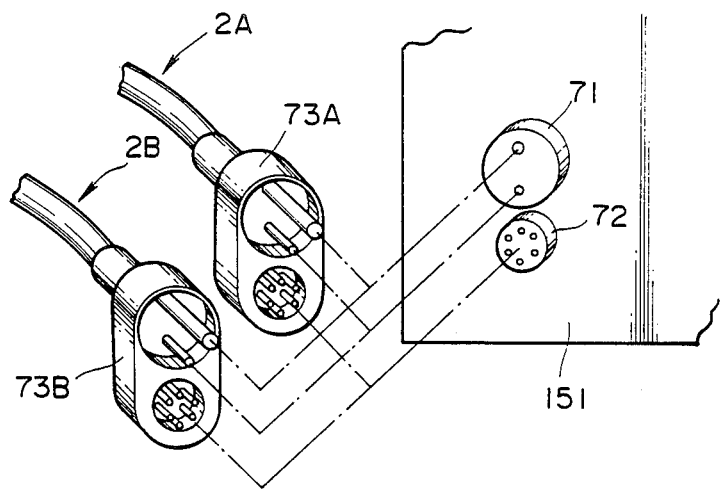

FIGS. 12 to 14 show the second embodiment of the present invention.

In this embodiment, by moving the rotary filter, the frame sequential type light source and white light source can be used in common.

In this embodiment, for example, on the front surface of the housing of a control apparatus 131, as shown in FIG. 14, a common light source connector receptacle 71 is provided and, below it, a signal connector receptacle 72 commonly used by the frame sequential type and color mosaic type is provided.

On the other hand, the connector 73A of the frame sequential type electronic scope 2A and the connector 73B of the color mosaic type electronic scope 2B can be fitted in the light source connector parts both to the connector receptacle 72. Though not shown in FIG. 14, the electronic scopes 2C and 2D fitted respectively with the frame sequential type and mosaic type television cameras is also the same. Also, by connecting the connector of the fiber scope 2E to the light source connector receptacle 71, a naked eye observation can be made.

In the light source apparatus 15c contained within the control apparatus 131 in this embodiment, as shown in FIGS. 12 and 13 a rotary filter part 133b consisting of a rotary filter 33a, a motor 32a rotating and driving it and a rotary position sensor 51a is movable along rails 134.

The above mentioned rotary filter part 133 is usually set in one end part of the rails 134 and, as shown, for example, in FIG. 13, when the rotary filter 33a is retreated from the light path of the light source lamp 31 and lens 34, a white light source part will be formed. On the other hand, when the rotary filter part 133 is moved to the lower side of the rails 134, it will be interposed in the course of the light path as shown in FIG. 12 to form a frame sequential type light source part.

Now, the above mentioned rotary filter part 133 is controlled in the movement by the movement controlling circuit 135 which is operated by the discriminating signal of the discriminating circuit 28. In this embodiment, when it is discriminated to be a frame sequential type scope by a type signal by the type signal generating circuit 27A or 27C, in the discriminating circuit 28a, a movement controlling instruction will be output in the movement controlling circuit 135 and the rotary filter part 133 will be moved from the state shown in FIG. 13 to the state shown in FIG. 12.

On the other hand, in case, the connector of the mosaic type scope 2B or 2D is connected, the rotary filter part 133 will be in the state shown in FIG. 13 and a white light will be fed. Also, in case the fiber scope 2E is fitted, a white light will be fed to the connector of the fiber scope.

When the frame sequential type scope 2A or 2C is fitted and then removed, the rotary filter part 133 will be returned to be retreated from the light path.

The others are of the same formation as is shown in FIG. 9.

According to this second embodiment, the light source part is used in common for the frame sequential type and the white light. Therefore, without providing two sets of the light source part, the frame sequential type or mosaic type scope or fiber scope can be switched. In the case of misconnecting the connector of the fiber scope to the frame sequential type side by mistake can be prevented. This is easy to use.

The above mentioned rotary filter part 133 may be manually moved.

Also, in this embodiment, without using the output circuit 80, the output end may be separate for the frame sequential type and mosaic type.

Figure 15:
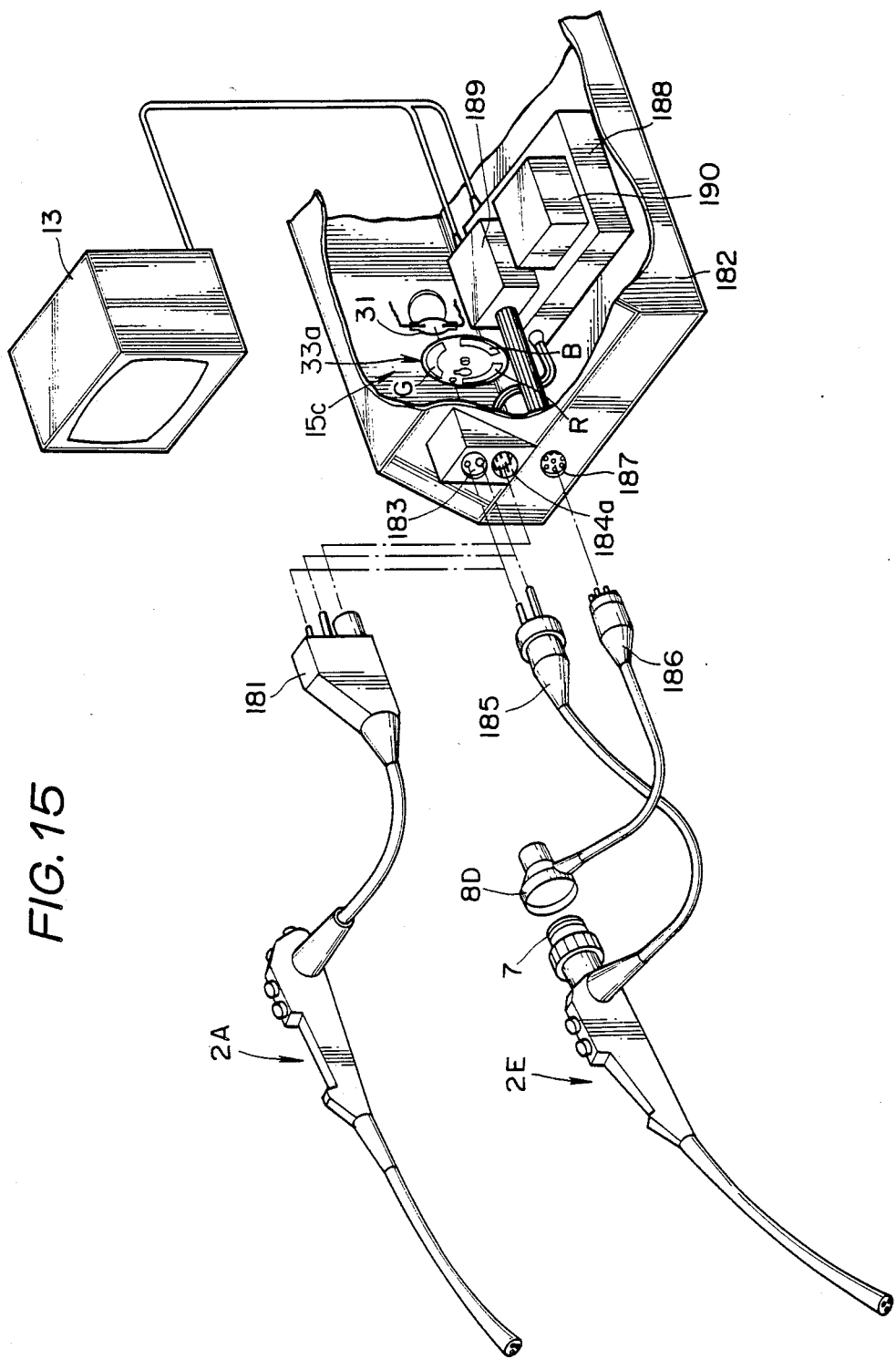
FIG. 15 is a perspective view showing an endoscope apparatus relating to a modification of the second embodiment.

Also, the video processor side may be of such formation such as is shown in FIG. 2 and the signal connector receptacles may be separately provided, for example, as shown in FIG. 15. In the example shown in FIG. 15, for example, a frame sequential type electronic scope 2A, a fiber scope 2E and a mosaic type television camera 8D which can be connected to this fiber scope 2E are shown.

A connector 181 of the above mentioned frame sequential type electronic scope 2A integrates a light source connector and a signal connector and can be connected to the light source connector receptacle 183 and frame sequential type connector receptacle 184a of the control apparatus 182.

The rotary filter 33a and light source lamp 31 are arranged inside the above mentioned light source connector receptacle 183.

Figure 16:
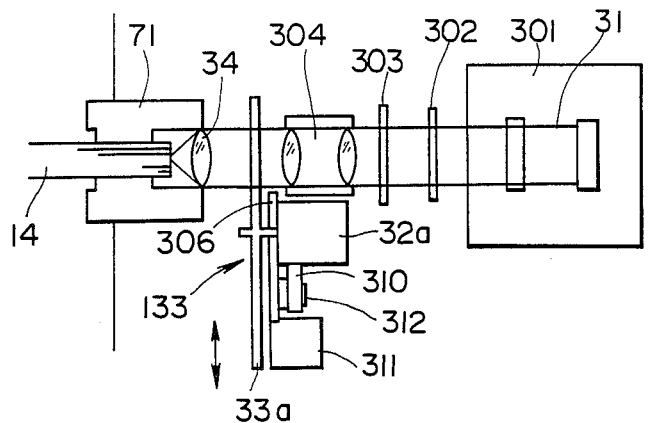
FIGS. 16 and 17 are respectively an explanatory view and perspective view showing an example of a concrete formation of a light source apparatus in the second embodiment.
Figure 17:
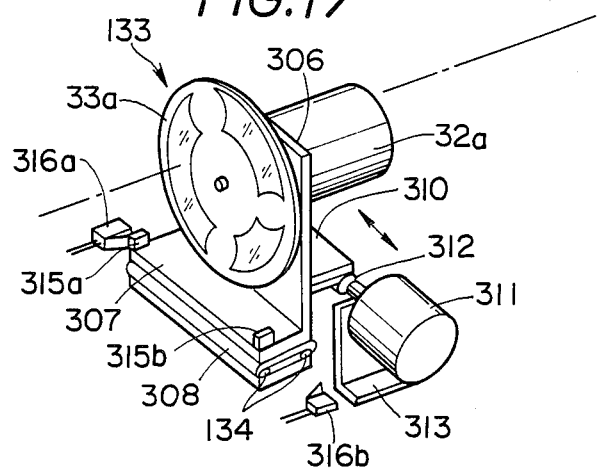

FIGS. 16 and 17 show an example of the concrete formation of a light source apparatus in the second embodiment.

As shown in FIG. 16, the white light emitted from the light source lamp 31 contained within a lamp house 301 is transmitted through a color filter 302 and diaphragm 303 and a condenser lens 302, is then transmitted through a rotary filter 33a, is condensed by a condenser lens 34 and enters the light guide 14 of the scope fitted to the light source connector receptacle 71.

The above mentioned rotary filter 33a and the motor 32a rotating and driving it are moved by a mechanism such as is shown in FIG. 17. That is to say, the above mentioned motor 32a is fitted to a plate-like fitting bracket 306 below which a horizontally bent flange part 307 is formed. Below this flange part 307, two rails 134 fixed to the housing side of the control apparatus are provided parallelly. In the bottom of the above mentioned flange part 307, a sliding part 308 in the form of holding these rails 134 from the right and left is formed. This sliding part 308 slidably fits the above mentioned rails 134 so that the rotary filter part 133 consisting of the above mentioned rotary filter 33a, motor 32a and rotary position sensor, not illustrated, may be movable.

On the surface on the light source lamp 31 side of the above mentioned fitting bracket 306, a rack gear 310 is fitted along the moving direction of the above mentioned rotary filter part 133. A worm gear 312 rotated by a motor 311 is meshed with this rack gear 310. The rotary motor 311 is fixed on the housing side of the control apparatus by a bracket 313. By normally and reversely rotating the above mentioned motor 311, the above mentioned rotary filter part 133 is made movable through the above mentioned worm gear 312 and rack gear 310. The above mentioned motor 311 is controlled by a movement controlling circuit 135 shown, for example, in FIG. 12.

On the upper surfaces of both end parts in the moving direction of the flange part 308 of the above mentioned fitting bracket 307, flat prismatic switch pressing parts 315a and 315b are provided to project. Switching position detecting microswitches 316a and 316b are arranged in the positions pressed by the above mentioned switch pressing parts 315a and 315b at both ends of the moving range of the above mentioned rotary filter part 133. When these microswitches 316a and 316b are pressed by the above mentioned switch pressing parts 315a and 315b, it will be sensed that the above mentioned rotary filter part 133 has reached the end of the moving range, the rotation of the above mentioned motor 311 will be stopped and the moving range of the rotary filter part 133 will be regulated. In the illustrated example, when the switch pressing part 315a presses the microswitch 316a, the white light from the light source lamp 31 will pass though the rotary filter 33a and will enter the light guide 14 as a frame sequential illuminating light. On the other hand, when the switch pressing part 315b presses the microswitch 316b, the white light from the light source lamp 31 will enter the light guide 14 without passing through the above mentioned rotary filter 33a.

Figure 18:
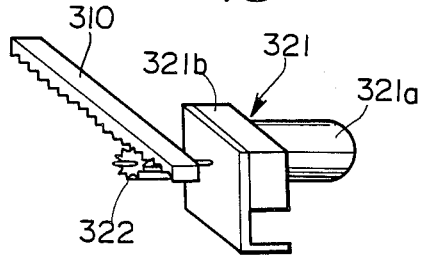
FIG. 18 is a perspective view showing a modification of FIG. 17.

As shown in FIG. 18, instead of the combination of the above mentioned rack gear 310 and worm gear 312, by using the rack gear 310 and a pinion 322 meshing with this rack gear 310 and rotated and driven by a gear motor 321 consisting of a motor 321a and a reduction gear 321b reducing the speed of the rotary output of this motor 321a, the above mentioned rotary filter part 133 may be moved.

Figure 19:
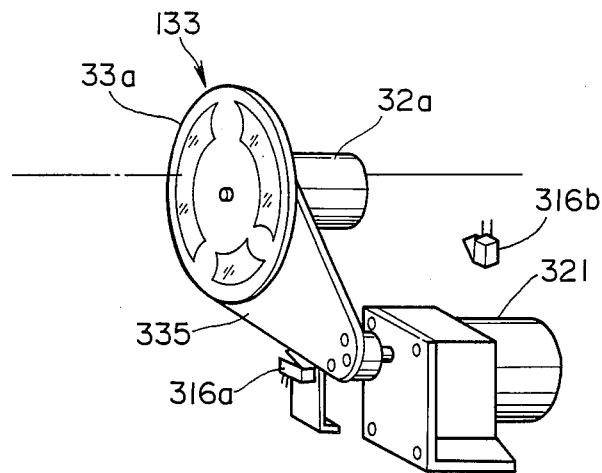
FIGS. 19 and 20 are perspective views showing a modification of a moving mechanism of a rotary filter part in the second embodiment.

FIG. 19 shows a modification of the moving mechanism of a rotary filter part.

In this example, a rotary filter part 133 is fitted to the expanded diameter side of a substantially fan-shaped fitting bracket 335 which is fitted in the small diameter side end part to the output shaft of a gear motor 321 so that, by normally and reversely rotating the gear motor 321, the above mentioned fitting bracket 335 and the rotary filter part 133 fitted to it may be rotated. Microswitches 316a and 316b sensing that the end of the rotating range has been reached when pressed by the side in the rotating direction of this fitting bracket 335 are arranged at both ends of the rotating range of the above mentioned fitting bracket 335. In the illustrated example, when the microswitch 316a is pressed, the white light from the light source lamp 31 will pass through the rotary filter 33a. On the other hand, when the microswitch 316b is pressed, the white light from the light source lamp 31 will enter the light guide 14 without passing through the above mentioned rotary filter 33a.

Figure 20:
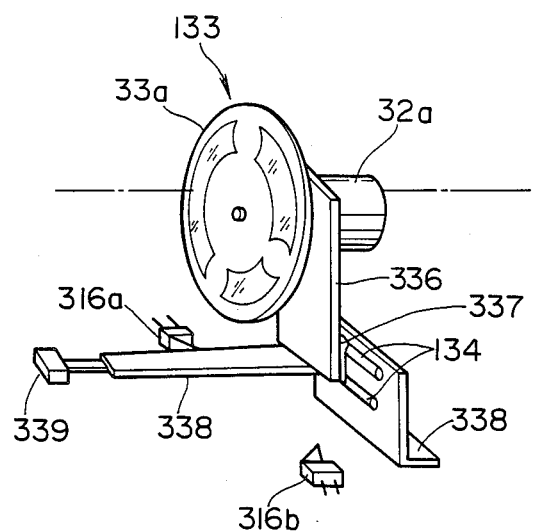

FIG. 20 shows another modification of the moving mechanism of the rotary filter.

In this example, the rotary filter part 133 is fitted to a fitting bracket 336. On the surface on the light source lamp 31 side of this fitting bracket 336, there is provided a sliding part 337 slidably fitted to rails 134 fixed to a body fitting bracket 338 fixed on the housing side of the control apparatus. The rotary filter part 133 fitted to the above mentioned fitting bracket 336 is made movable along the above mentioned rails 134. A lever 338 is extended in the light progressing direction from the light source lamp 31 and is provided in the tip part with a grip 339 which is projected out of the front surface of the housing, for example, of the control apparatus 131 to be gripped to move the above mentioned lever 338 in the rotary filter part 133 moving direction so as to be able to move manually the above mentioned rotary filter part 133. Miroswitches 316a and 316b sensing that the end of the moving range has been reached when pressed by the side in the moving direction of this lever 338 are arranged in both end parts of the moving range of the above mentioned lever 338. In the illustrated example, when the microswitch 316a is pressed, the white light from the light source lamp 31 will pass through the rotary filter 33a1 and will enter the light guide. On the other hand, when the microswitch 316b is pressed, the white light from the light source lamp 31 will enter the light guide without passing through the above mentioned rotary filter 33a.

Figure 21:
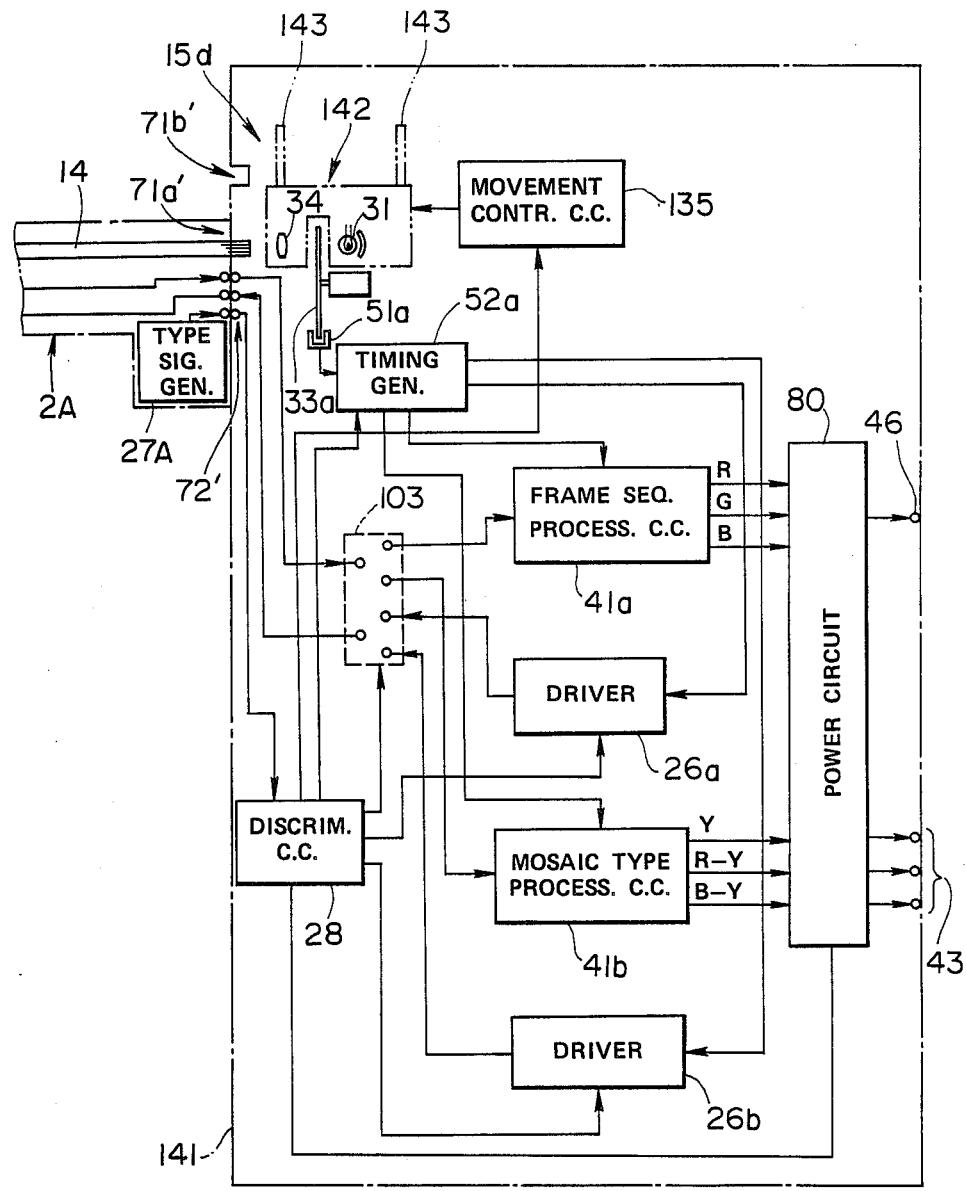
FIGS. 21 and 22 relate to the third embodiment of the present invention.
Figure 22:
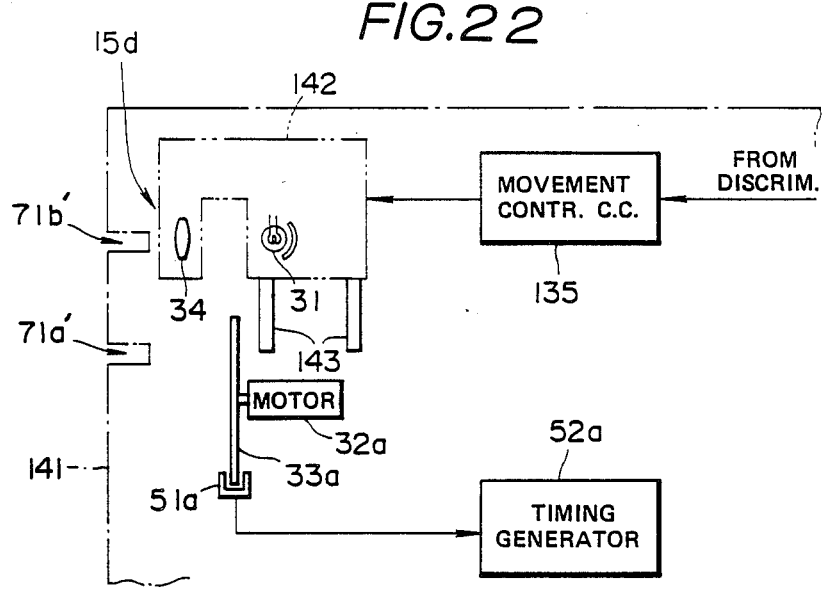

FIGS. 21 and 22 show the fourth embodiment of the present invention.

In this embodiment, by moving the light source lamp, the frame sequential type light source and the white light source can be used in common.

In this embodiment, on the front surface, for example, of the housing, as shown, for example, in FIG. 11, the common signal connector receptacle 72' is provided and, near it, the frame sequential type light source connector receptacle 71a' and white light source connector receptacle 71b' are provided In the light source apparatus 15d contained within the control apparatus 141 in this embodiment, as shown in FIGS. 21 and 22, the light source part 142 consisting of the light source lamp 31 and condenser lens 34 is movable along the rails 143.

The above mentioned light source part 142 is normally set in one end part of the rails 143. As shown, for example, in FIG. 22, when the rotary filter 33a is not interposed in the light path of the light source lamp 31 and condenser lens 34, a white light source part will be formed. In this case, the white light from the above mentioned light source lamp 31 will enter the light guide 14 of the color mosaic type scope 2B or 2D or fiber scope 2E fitted to the light source connector receptacle 71b' without passing through the rotary filter 331. On the other hand, when the light source part 142 is moved to the lower side of the rails 143 from this state, as shown in FIG. 21, the rotary filter 33a will be interposed in the light path of this light source part 142 and a frame sequential type light source part will be formed. In this case, the white light from the above mentioned light source lamp 31 will pass through the rotary filter 33a and will enter the light guide 14 of the frame sequential type scope 2A or 2C fitted to the light source connector receptacle 71a'.

The moving mechanism of the above mentioned light source part 142 may be the same as the moving mechanism of the rotary filter part shown in FIGS. 16 to 20.

Now, the above mentioned light source part 142 is controlled in the movement by the movement controlling circuit 135 which is operated by the discriminating signal of the discriminating circuit 28. In this embodiment, when it is discriminated to be a frame sequential type scope by the type signal by the type signal generating circuit 27A or 27C, a movement controlling instruction will be output to a movement controlling circuit 135 from the discriminating circuit 28 and the light source part 142 will be moved from the state shown in FIG. 22 to the state shown in FIG. 21.

On the other hand, in case the connector of the mosaic type scope 2B or 2D is connected, the light source part 142 will be in the state shown in FIG. 22 and a white light will be fed. Also, in case the fiber scope 2E is fitted, a white light will be fed to the connector of the fiber scope.

The others are the same as of the formation shown in FIG. 9. The same as in the second embodiment, the light source part is used in common. Therefore, without providing two sets of the light source part, the frame sequential type or mosaic type scope or fiber scope can be accommodated.

In this embodiment, the connector receptacle may be moved together with the light source part 142. With such a formation, the connector receptacle will be one.

Also, in this embodiment, a manually movable structure can be made.

Also, in this embodiment, without using the output circuit 80, the output ends may be made separate for the frame sequential type and mosaic type.

The video processor side may be formed as shown in FIG. 2 and the signal connector receptacles may be separately provided for the frame sequential type and mosaic type. In such a case, the connector receptacle will be of a formation such as is shown, for example, in FIG. 5 or 8.

Figure 23:
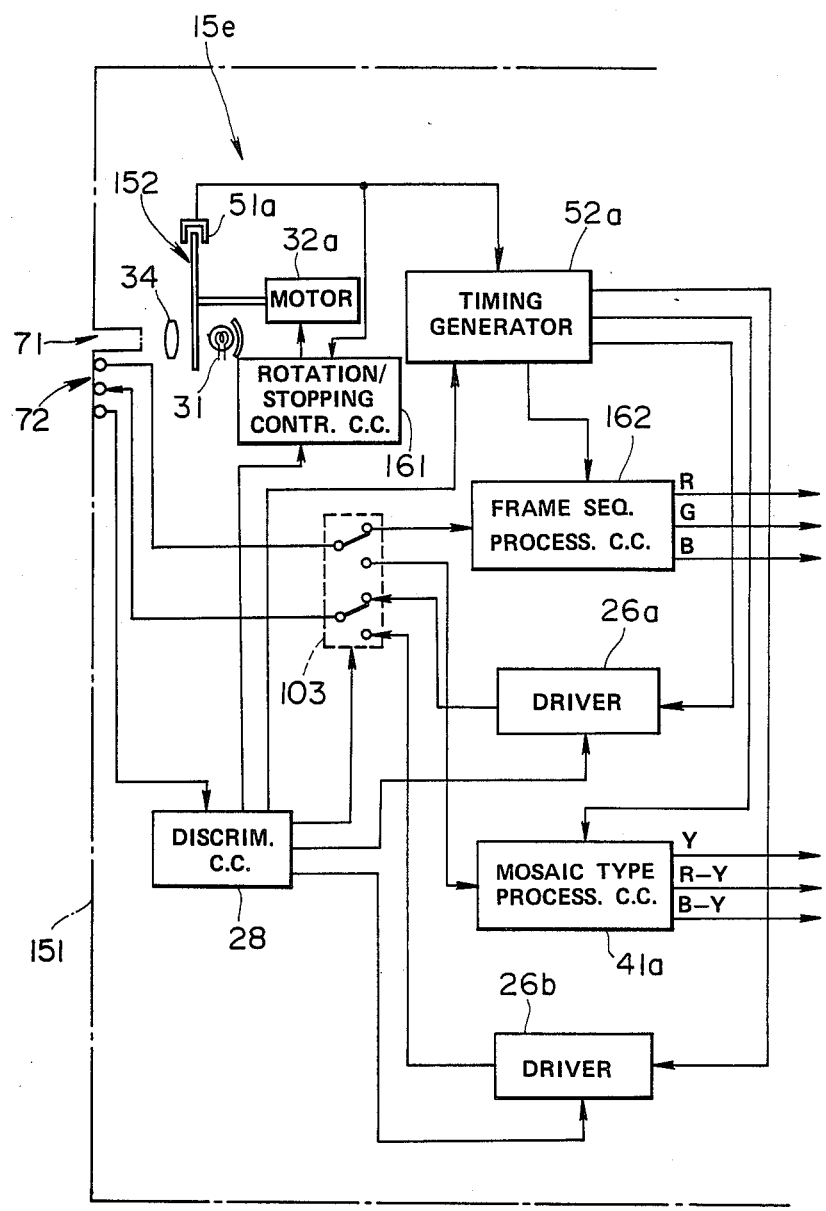
FIGS. 23 to 25 relate to the fourth embodiment of the present invention.
Figure 24:
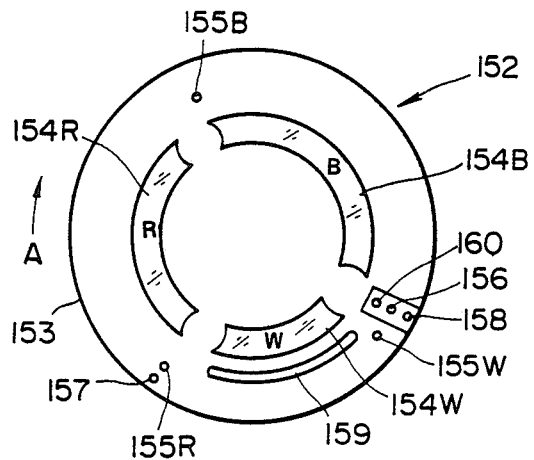
Figure 25:
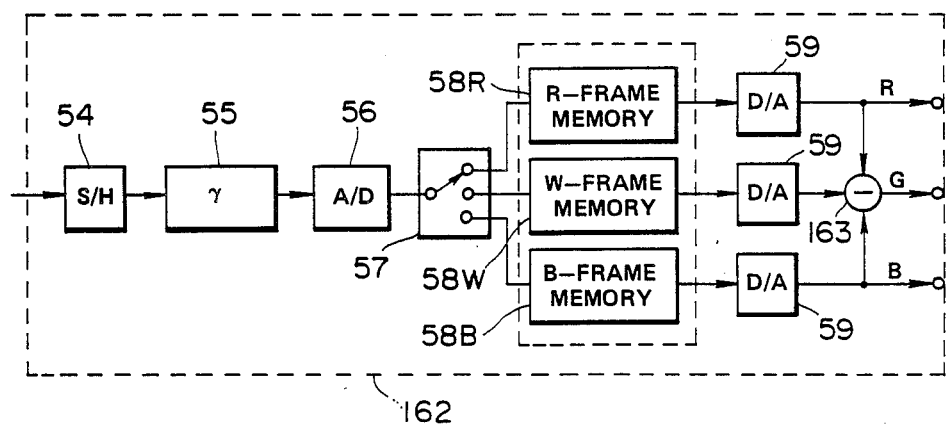

FIGS. 23 to 25 show the fourth embodiment of the present invention.

In this embodiment, when the frame sequential illuminating lights are made R, W (white light) and B instead of R, G and B, the frame sequential type light source and white light source can be commonly used.

In the light source apparatus 15e contained within the control apparatus 151 in this embodiment, for the rotary filter 152 used for the frame sequential illumination with the illuminating lights of the above mentioned R, W and B, as shown in FIG. 24, a disc-like filter frame 153 is provided with fan-shaped windows fitted respectively with R, W and B color transmitting filters 154R, 154W and 154B transmitting respectively R, W and B. This W transmitting filter 154W is a filter transmitting R, G and B. (It may be made an approximately transparent plate to transmit all the white light.)

The respective R, W and B color transmitting filters 154R, 154W and 154B are adjusted in the arcuate length so that the illuminating period may be different in response to the photosensitive characteristics of the solid state imaging device 18 or 22.

In the above mentioned filter frame 153, respective lead pulse (detecting) holes 155R, 155W and 155B are provided near the ends (with respect to the rotating direction A) of the R, W and B color transmitting filters 154R, 154W and 154B so as to be able to detect the lead time just after the illumination with respective R, W and B. The positions of these lead pulse holes 155r, 155W and 155B can be detected by the fact that, in case the position opposed to the photosensor 156 arranged as opposed to the light emitting device to hold the filter frame 153 is reached, the light of the light emitting device will be received in the pulse-form in the photosensor 156. When this pulse-form light is detected, the detecting signal will be transmitted to the timing generator 52a and a read-out driving pulse will be applied to the solid state imaging device 18 or 22 through the driver 26a or 26b.

In the above mentioned filter frame 153, a start pulse hole 157 is provided in the position adjacent radially, for example, to the lead pulse hole 155R. When this position reaches the position opposed to the photosensor 158, the photosensor 158 will output a start pulse. Further, in order to detect the position of the W color transmitting filter 154W, an arcuate slot 159 is formed arcuatly in the peripherally outside position of this color transmitting filter 154W. By detecting this slot 159 with the photosensor 160, the position of the W color transmitting filter 154W can be detected. The output of this photosensor 160 controls the stopping position of the rotary filter 152. That is to say, in case the motor 32a rotating and driving the rotary filter 152 is not rotating and driving, so that the stopping position of the rotary filter 152 may be the position of the slot 159 opposed to the photosensor 160, the output of the photosensor 160 will be input into a rotation/stop controlling apparatus 161 to control the stopping position of the rotary filter 152. In this stopping position state, the illuminating light of the light source lamp 31 passes through the W color transmitting filter 150W, is opposed to the light source connector receptacle 71 and can feed a white illuminating light. When the fiber scope is connected to the connector receptacle 71 and nothing is connected to the connector receptacle 72 or nothing is connected to either of the connector receptacles 71 and 72 (these both states can be detected by sensing the high impedance state with the discriminating circuit) or when the mosaic type scope is connected, this white illuminating state will be made.

On the other hand, when the frame sequential type scope is connected, the connection will be sensed by the discriminating circuit 28, an instruction signal for rotating and driving the motor 32a is output to the rotation/stop control circuit 161 to rotate and drive the motor 32a and to make a frame sequential illumination state.

In this embodiment, the light source connector receptacle 71 of the imaging apparatus body 151 is commonly used for the white light and frame sequential type. Also, for example, as shown in FIG. 14, the signal connector receptacle is commonly used by the frame sequential type and mosaic type. In FIG. 14, two electronic scopes 2A and 2B are shown but any other scopes 2C, 2D and 2E can be connected.

Now, in this embodiment, as the frame sequential illuminating lights are not of R, G and B, the frame sequential process circuit 162 is of a formation such as is shown, for example, in FIG. 25. That is to say, in the process circuit 41a shown in FIG. 6, the W frame memory 58W is replaced instead of the G frame memory 58G. (Though the memory contents are different, the same frame memory can be used as a hardware.) Further, the W signal read out of the W frame memory 58W and made an analogue signal by the D/A converter 59 is input into a deductor 163 and has the R color signal and B color signal deducted to produce a G color signal. The others are the same as in the process circuit 41a shown in FIG. 6.

The control apparatus 151 shown in the above mentioned FIG. 23 is substantially the same as in FIG. 9 in the other formations.

According to this embodiment, both of the frame sequential type and mosaic type commonly use the light source part. If only the scope is connected, it can be used conveniently. Any moving means for moving the light source part and rotary filter part need not be newly provided, the cost can be reduced and the size can be made small.

In the above mentioned embodiment, the frame sequential illumination is made with R, W and G. However, it is not limited to this. The illumination can be made, for example, with R, G, W; W, G, B; Cy (cyanine), Ye (yellow), W; Cy, W, Mg (magenta); or W, Ye, Mg.

In this embodiment, the output end may be made common to the frame sequential type and mosaic type.

The video processor side may be made of such formation as is shown in FIG. 1 and the signal connector receptacles may be separately provided for the frame sequential type and mosaic type. In such a case, the connector receptacle will be of a formation such as is shown, for example, in FIG. 15.

When a fiber scope is connected to the connector receptacle 71 but nothing is connected to the connector receptacle 72, a picture image showing that a fiber scope observation is being made may be displayed.

Figure 26:
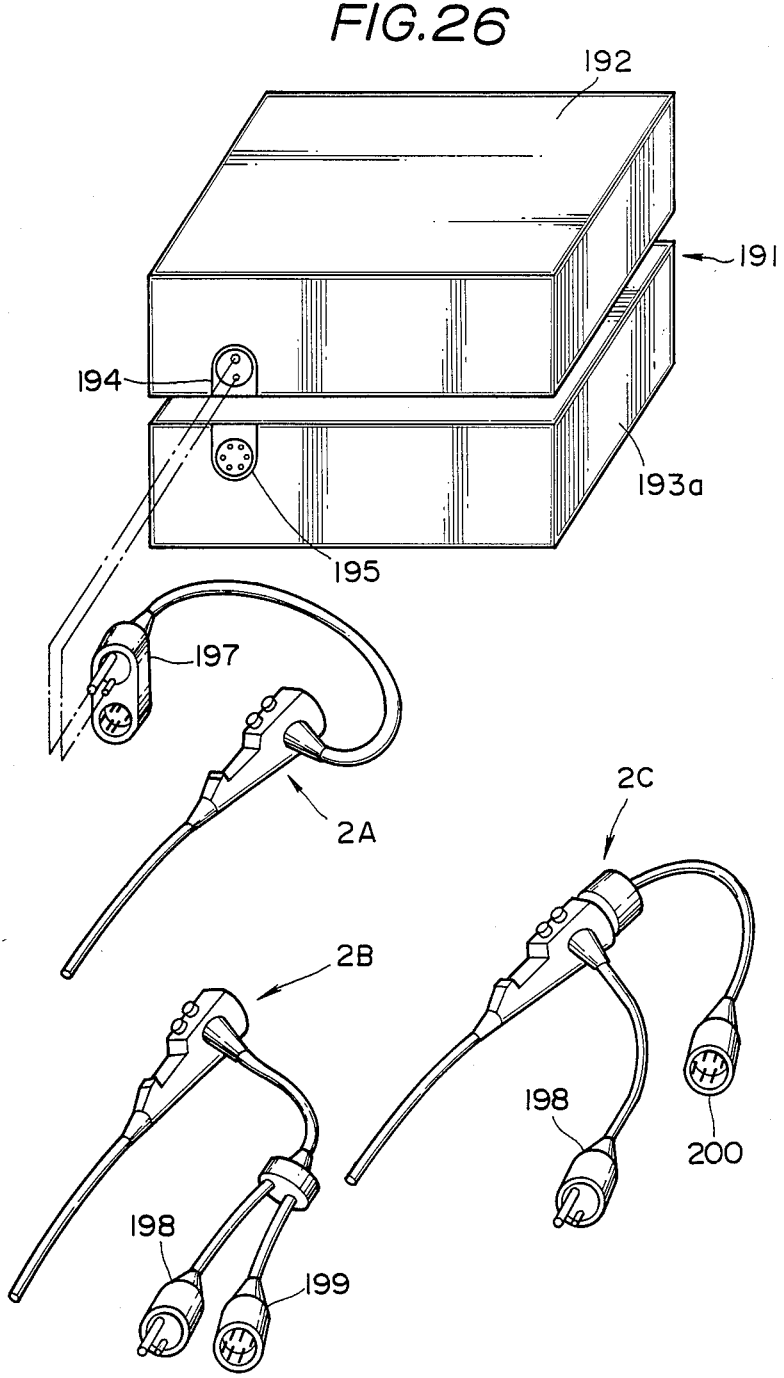
FIGS. 26 to 28 relate to the fifth embodiment of the present invention.
Figure 27:
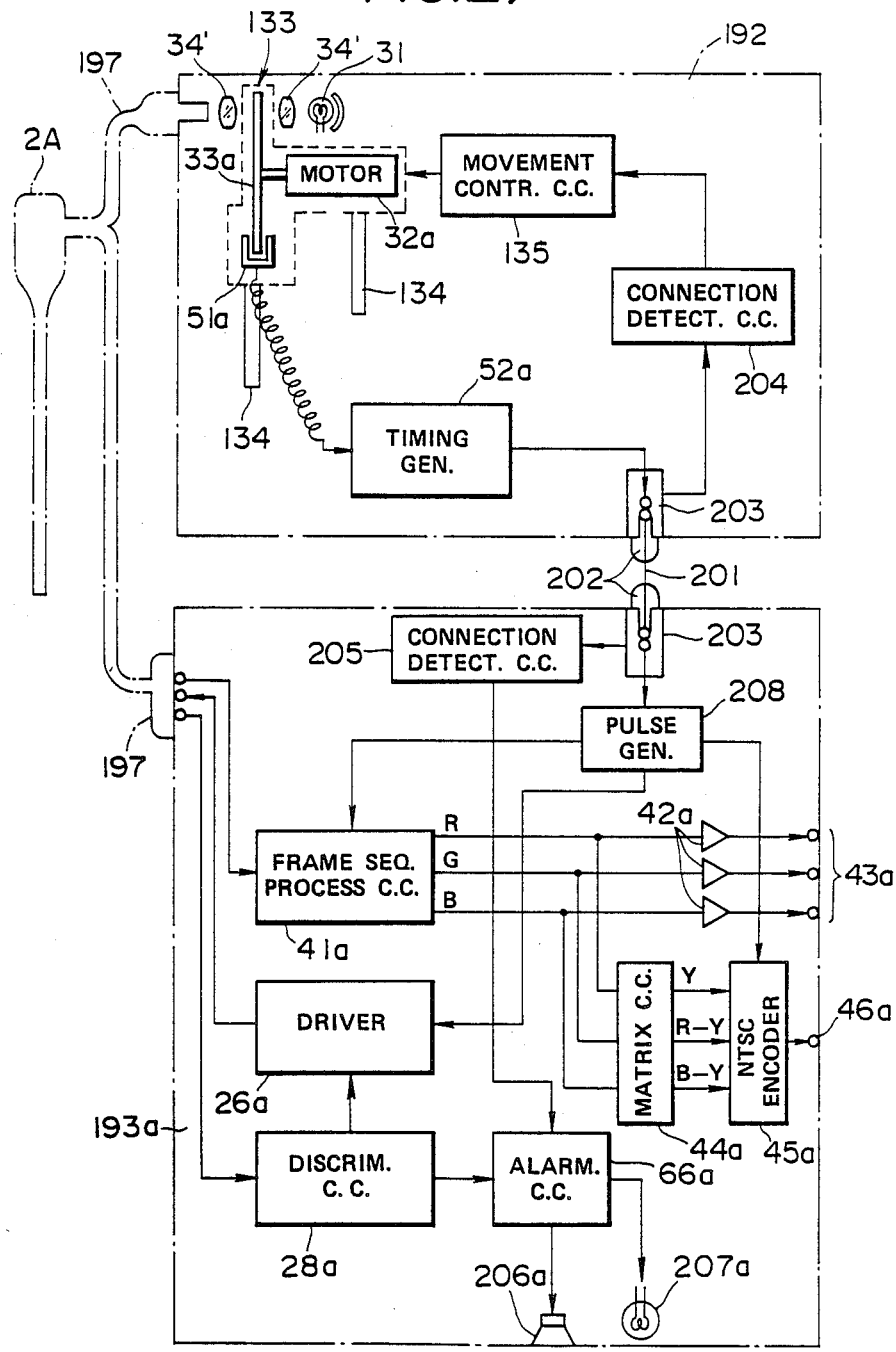
Figure 28:
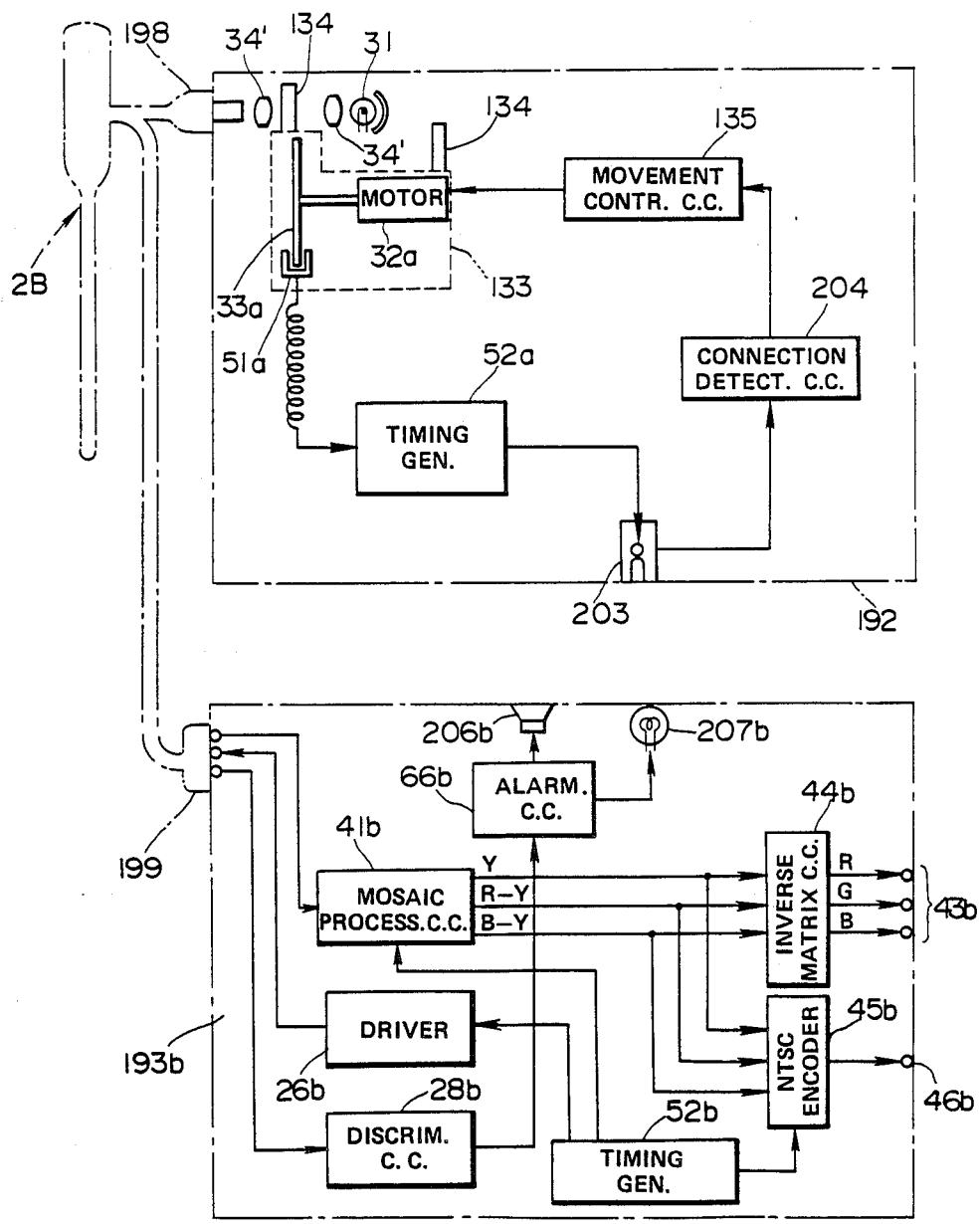

FIGS. 26 to 28 show the fifth embodiment of the present invention.

In this embodiment, a control apparatus 191 is formed of a light source apparatus 192 made separate and commonly used for all scopes and a frame sequential type video processor part 193a shown in FIGS. 26 and 27 or a mosaic type video processor part 193b shown in FIG. 28. As shown in FIG. 26, a light source connector receptacle 194 is provided on the lower side of the front surface of the light source part 192. On the other hand, a signal connector receptacle 195 is provided on the upper side of the front surface of each video processor part 193a or 193b. Both connector receptacles 194 and 195 are provided to be adjacent to each other above and below when the light source part 192 is overlapped on the upper surface of the video processor part 193a or 193b (in FIG. 26, one video processor part 193a is shown).

On the other hand, in the frame sequential type electronic scope 2A, its connector 197 integrates the light source connector part and signal connector part and, as shown in FIG. 26, when the light source apparatus 192 and video processor part 193a are overlapped on each other, both connector receptacles 194 and 195 can be connected.

On the other hand, for example, in the mosaic type electronic scope 2B, its connector is divided into a light source connector 198 and signal connector 199 which can be connected respectively to connector receptacles 194 and 195. For example, on the fiber scope 2C fitted with the frame sequential type television camera, the light source connector 198 and signal connector 200 can be connected respectively to the connectors 194 and 195.

Now, the above mentioned light source apparatus 192 is of a formation similar to that of the light source apparatus 15c in FIGS. 12 and 13. The lens 34 in FIGS. 12 and 13 is made two lenses 34' in this embodiment.

This light source apparatus 192 is provided with a connector receptacle 208 to connect one of the connectors 202 of a cable 201 to feed a timing pulse or the like of a timing generator 52a to a separate frame sequential type video processor part 193a. Likewise, the frame sequential type video processor 193a is also provided with the connector receptacle 203.

The above mentioned light source apparatus 192 is provided with a connection sensing circuit 204 sensing whether the connector 202 of the signal cable 201 is connected to the connector receptacle 203 or not. As shown in FIG. 27, when the cable 201 is connected, by the output of this circuit 204, a movement instructing signal will be output to the movement controlling circuit 135, the rotary filter 133 will be moved along the rails 134 and the rotary filter 33a will be interposed in the illuminating light path to make a frame sequential illumination.

On the other hand, a connection sensing circuit 205 sensing whether the connector 202 of the cable 201 is connected to the connector receptacle 203 or not is provided also within the frame sequential type video processor part 193a. The output of this sensing circuit 205 is input into a warning circuit 66a. When it is sensed from the discriminating circuit 28a that the frame sequential type scope 2A or 2C is connected and a sensing signal showing that the cable 201 is not connected is input from the connection sensing circuit 205, it will be warned by a warning buzzer 206a and a warning light 207a that the cable 201 is not connected. Also, in case the signal connector 199 of the mosaic type scope 2B or 2D is connected to the signal connector receptacle 195, it will be warned.

With the above mentioned cable 201, the timing pulse from the light source apparatus 192 outputs a control signal to the driver or the like through the pulse generator 208 within the video processor part 193a. The other formations are the same as of the video processor 25a shown in FIG. 2.

The formation of the mosaic type video processor part 193b shown in FIG. 28 is similar to that of the video processor 25b shown in FIG. 2.

The above mentioned video processor part 193b is provided with a warning circuit 66b operated by the output of the discriminating circuit 28b. When the signal connector of the frame sequential type scope 2A or 2C is connected to the mosaic type signal connector receptacle 195, this warning circuit 66 will sense the mis-connection and will warn it with a buzzer 206b or warning light 207b.

The others are of the same formation as is shown in FIG. 2.

In case the above mentioned mosaic type scope 2B or 2D or fiber scope 2E is connected, the rotary filter part 133 will not be moved and therefore the white light of the light source lamp 31 will be condensed and radiated to the connector 198 through the lenses 34.

According to this embodiment, the frame sequential type or mosaic type scope or fiber scope can be accommodated with one unit of a light source apparatus 192. Also, as in the illustrated example, a video processor part 193a or 193b corresponding to the scope to be used can be selected and used as combined with the above mentioned light source apparatus 192 and can be used also in the case of using another video processor not combined with this light source apparatus.

FIG. 27 shows the frame sequential type electronic scope 2B as connected. Its connector 197 is divided for the sake of convenience.

In the above mentioned embodiment, even if the connector is made integral as in the case of the frame sequential type scope 2A or is separated as in the case of the mosaic type scope 2B, it can be connected.

In FIG. 26, the connector 197 of the frame sequential type electronic scope 2A is made integral for the light source and for the signal but may be separated as in the case of the mosaic type electronic scope 2B. On the contrary, the connectors 198 and 199 of the mosaic type electronic scope 2B may be made integral.

In above mentioned connection sensing circuit 204 and 205 had better be there but are not always necessary.

Also, in the above mentioned embodiment, the rotary filter part 133 is made movable but, as in the third embodiment shown in FIGS. 21 and 22, the frame sequential type light source and white light source connector receptacles may be separately provided and the light source lamp 31 and lenses 34' may be made movable.

Also, the light source connector receptacle may be made common and the light source lamp 31, lenses 34' and connector receptacle 194 parts may be made movable.

In the light source apparatus 192, the rotary filter part 133 may be moved not by the output of the connection sensing circuit 204 but manually.

Figure 29:
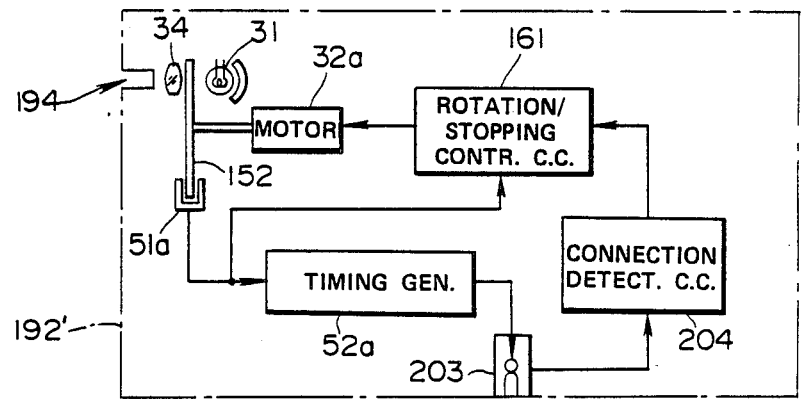
FIG. 29 is a block diagram showing the formation of a light source apparatus relating to the sixth embodiment of the present invention.

FIG. 29 shows the sixth embodiment of the present invention.

In this embodiment, the same as in the fifth embodiment, in a light source apparatus 192' commonly used for the frame sequential type light source and for the white light source, the rotary filter 152 shown in FIG. 24 is used as the rotary filter of the rotary filter part 133 in FIG. 27, is not of a movable structure and is controlled in the rotation/stop by the rotation/stop controlling circuit 161 (See FIG. 23). In this case, the frame sequential type process circuit 162 shown in FIG. 25 is used instead of the frame sequential type process circuit 41a shown in FIG. 27.

The same as in the fifth embodiment, as shown in FIGS. 27 and 28, this optical source apparatus 192' can be used as combined with the frame sequential type video processor part 193a and mosaic type video processor part 193b.

According to this embodiment, the same as in the fifth embodiment, the frame sequential type or mosaic type scope or fiber scope can be accommodated with one unit of the light source apparatus 192'. No moving means for moving the light source part and rotary filter part is required, the cost can be reduced and the size can be made small.

Figure 30:
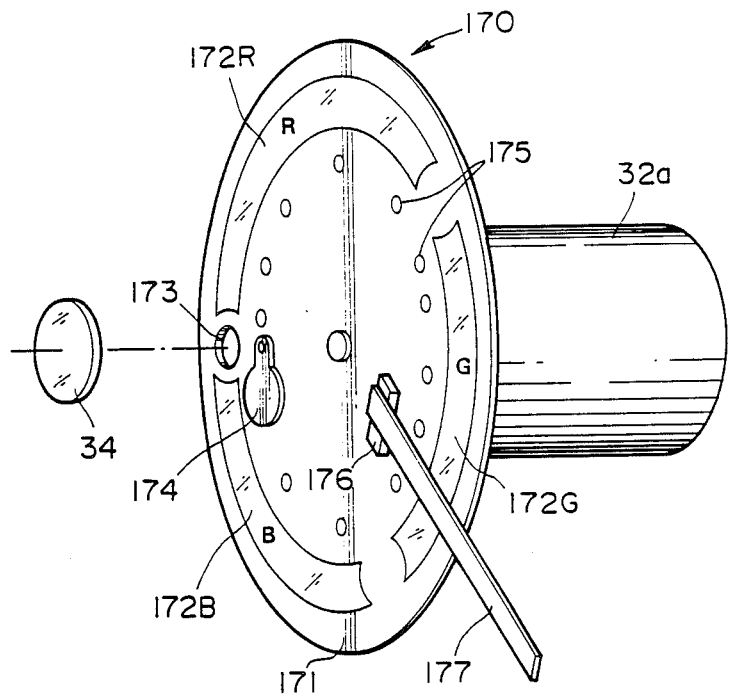
FIGS. 30 and 31 relate to the seventh embodiment of the present invention.
Figure 31:
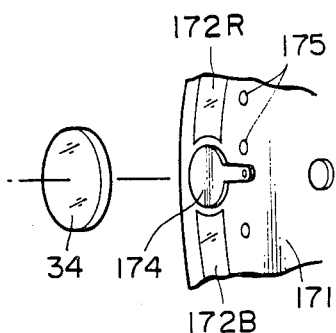

FIGS. 30 and 31 show the seventh embodiment of the present invention.

In this embodiment, as shown in FIG. 30, a filter frame 171 forming a rotary filter 170 is provided with R, G and B color transmitting filters 172R, 172G and 172B. A white illuminating hole 173 is made in a light intercepting part, for example, between the R and B color transmitting filters 172R and 172B1 and can intercept the light with a light intercepting plate 174 fitted rotatably with a position on a segment connecting this hole 173 and the center as a pivotal point.

That is to say, in the above mentioned light intercepting plate 174, when the filter frame 171 is rotated by the motor 32a, by the centrifugal force, as shown in FIG. 31, the direction connecting the center position of the disc-like light intercepting part and the pivotal point will coincide with the radial direction and, in this state, the hole 173 will be closed with the light intercepting plate 174 and ordinary R, G and B frame sequential illuminations can be made.

On the other hand, when the rotation is stopped, no centrifugal force will work and therefore, as shown in FIG. 30, the light intersecting plate 174 will retreat from the hole 173 under the gravity.

The above mentioned filter frame 171 is controlled in the position so that, when stopped, the hole 173 will be on the optical axis connecting the light source lamp and lens 34. For this position control or for detecting the timing of reading out the solid state imaging device signal in the case of the R, G and B frame sequence, many holes 175 are made in the peripheral direction in the filter frame 171 and a light emitting device and photosensor 176 are arranged on both sides of the plate of the filter frame 171 to form a position detecting rotary encoder. In FIG. 30, the photosensor 176 is fitted to the tip of the sensor fitting plate 177.

In this embodiment, the motor 32 is controlled in the rotation/stop by the rotation/stop controlling circuit 161 shown in FIG. 23. The video processor side can be of the same formation as, for example, in FIG. 23. However, the frame sequential type process circuit 41a shown in FIG. 6 is used instead of the frame sequential type process circuit 162.

As shown in FIG. 29, the light source apparatus may be made separate from the video processor.

According to this embodiment, no moving means for moving the light source part and rotary filter part is required, the light source lamp can be commonly used, the frame sequential illuminating lights are of ordinary R, G and B and such ordinary frame sequential process circuit as is shown in FIG. 6 can be used.

Figure 32:
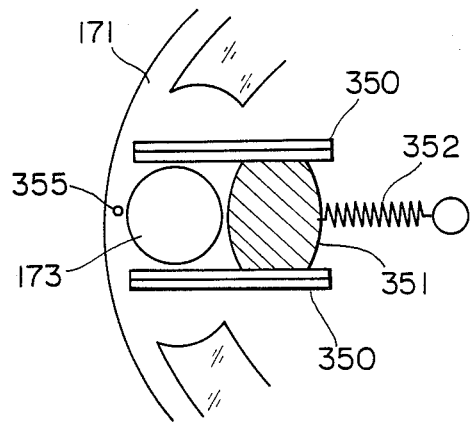
FIG. 32 is an explanatory view showing rotary filter relating to a modification of the seventh embodiment.

FIG. 32 shows a modification of the seventh embodiment.

In this example, two sliding plates 350 are extended in the radial direction of the filter frame 171 on both sides of the rotating direction of the hole 173 made in the filter frame 171. A light intercepting plate 351 of a size capable of covering the above mentioned hole 173 is slidably fitted in the radial direction of the filter frame 171 between these sliding plates 350. This light intercepting plate 351 is fitted at the other end of a spring 352 fixed at one end to the above mentioned filter frame 171 on the side nearer to center than this light intercepting plate 351 so as to be energized toward the center by this spring 352. A stopper pin 355 regulating the outward movement of the above mentioned light intercepting plate 351 is provided radially outside the filter frame 171 of the above mentioned hole 173.

When the filter frame 171 is rotated by the motor 32a, the above mentioned light intercepting plate 351 will move radially outward of the filter frame 171 against the energizing force of the above mentioned spring 352 by the centrifugal force and will close the above mentioned hole 173 so that ordinary R, G and B frame sequential illuminations may be made.

On the other hand, when the above mentioned filter frame 171 is stopped, the centrifugal force will not work, therefore, as shown in FIG. 32, the light intercepting plate 351 will be moved radially inward of the filter frame 171 by the above mentioned spring 352 and will be retreated from the above mentioned hole 173.

Figure 35:
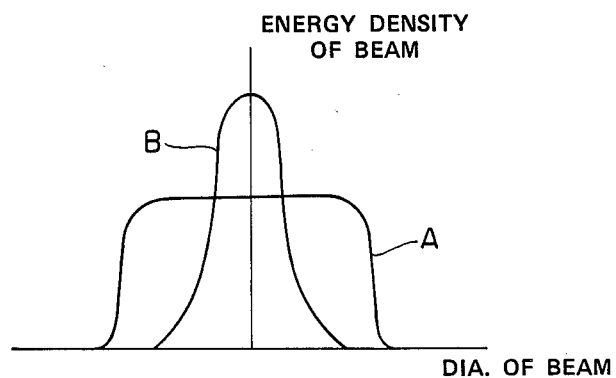
FIG. 35 is an explanatory view showing an energy density against the spot diameter of an illuminating light beam.

FIGS. 33 and 35 show the eighth embodiment of the present invention.

In this embodiment, in the illumination with the white light, the illuminating light condensed on the end surface of the light guide fiber bundle is defocused so that the light guide fibers may not be burned.

Figure 34:
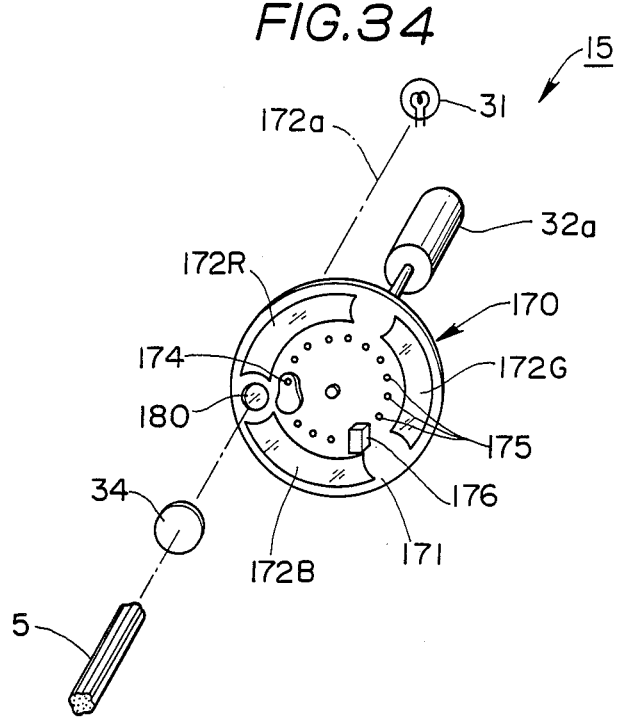
FIG. 34 is a perspective view explaining the formation of a light source apparatus.

In FIG. 34, the light source apparatus 15 is provided with a light source lamp 31 emitting a white light, a rotary filter 170 rotated and driven by a motor 32a and a condenser lens 34 condensing the lights having passed through this rotary filter 170.

The above mentioned rotary filter 170 has three primary colors of red (R), green (G) and blue (R) transmitting fan-shaped filters 172R, 172G and 172B in the peripheral direction of the filter frame 171. A concave lens 180 transmitting a white light is fitted in a hole opened, for example, between the blue (B) color transmitting filter 172B and the red (R) color transmitting filter 172R, A light intercepting plate 174 intercepting the white light by covering this concave lens 180 is pivoted on the filter frame 171 surface. Further, on the above mentioned filter frame 171, many holes 175 are provided as encoder indices in the peripheral direction. On both sides of the plate of this filter frame 171, for example, a light emitting device and photosensor 176 are arranged as a position sensor to form a position detecting rotary encoder.

Here, the optical axis 170a of the white light emitted form the above mentioned light source lamp 31 is made at right angles with the color transmitting filters 172R, 172G and 172B and concave lens 180, enters the condenser lens 34 through the above mentioned color transmitting filters 172R, 172G and 172B or the concave lens 180 and reaches the end surface of the light guide 5 consisting of a fiber bundle through this condenser lens 34.

Figure 33A:
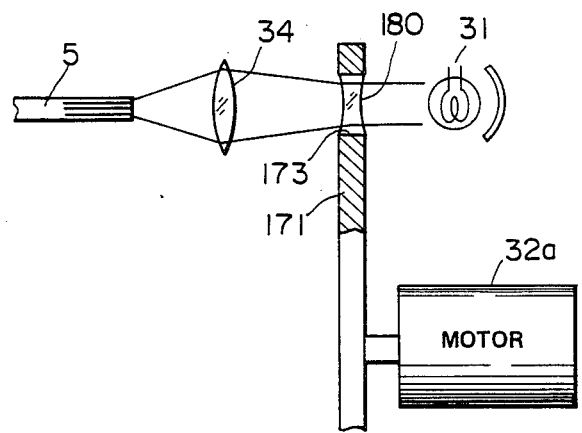
FIG. 33(a) is an explanatory view showing the formation of a light source apparatus when a color mosaic type electronic scope or fiber scope is fitted.

Now, as shown in FIG. 33(a), in case the fiber scope 2E or color mosaic type electric scope 2B requiring a white illumination is fitted to the control apparatus 1a, the concave lens 180 will be interposed in the above mentioned optical axis 170a connecting the light source lamp 31 and light guide 5 end surface. The white light emitted from the light source lamp 31 is defocused on the light guide 5 end surface through this concave lens 180. This means that the energy density of the illuminating light on the end surface of the light guide 5 consisting of a fiber bundle is dispersed as shown by the curve A in FIG. 35. Therefore, the fear of burning the light guide 5 end surface can be dissolved (for the above mentioned scopes 2E and 2B) and a proper illuminating light amount can be fed.

Figure 33B:
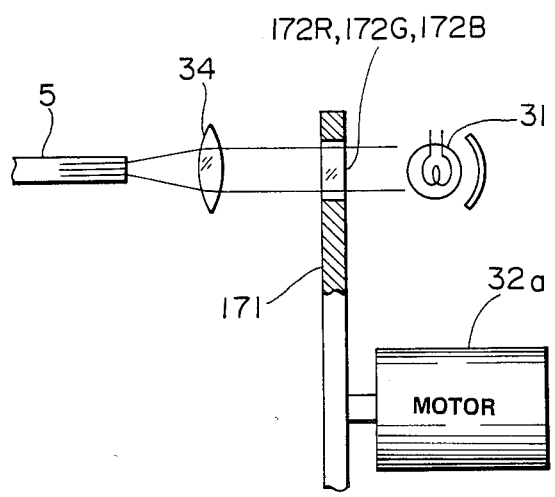
FIG. 33(b) is an explanatory view showing the formation of a light source apparatus when a frame sequential type electronic scope is fitted.

In case the frame sequential type electronic scope 2A is fitted to the control apparatus 1a, the above mentioned rotary filter 170 will be rotated and driven by a motor 32a and any of the color transmitting filters 172R, 172G and 172B will be interposed in the above mentioned optical axis 172a. As shown in FIG. 33(b), in case any of these color transmitting filters 172R, 172G and 172B is interposed, the white light emitted form the light source lamp 31 will be made an illuminating light of the respective color lights by the above mentioned color transmitting filters 172R, 172G and 172B and will be focused by the condenser lens 34 on the light guide 5 end surface. This means that the energy density of the illuminating light on the light guide 5 end surface concentrates as shown by the curve B in FIG. 35. The reduction of the illuminating light by passing through the color transmitting filters 172R, 172G and 172B can be compensated and a illuminating light of a proper light amount can be fed.

Therefore, in the eighth embodiment of the present invention, the concave lens 180 is provided on the same periphery of the filter frame 171 of the above mentioned rotary filter 170 as an illuminating light amount varying means so that, in the fiber scope 2E or color mosaic type electronic scope 2B using a white light as an illuminating light, the problem of burning the end surface of the light guide 5 can be solved through the concave lens 80. In the frame sequential type electronic scope 2A, the light reduction by passing through the color transmitting filters 172R, 172G and 172B can be compensated.

Figure 36:
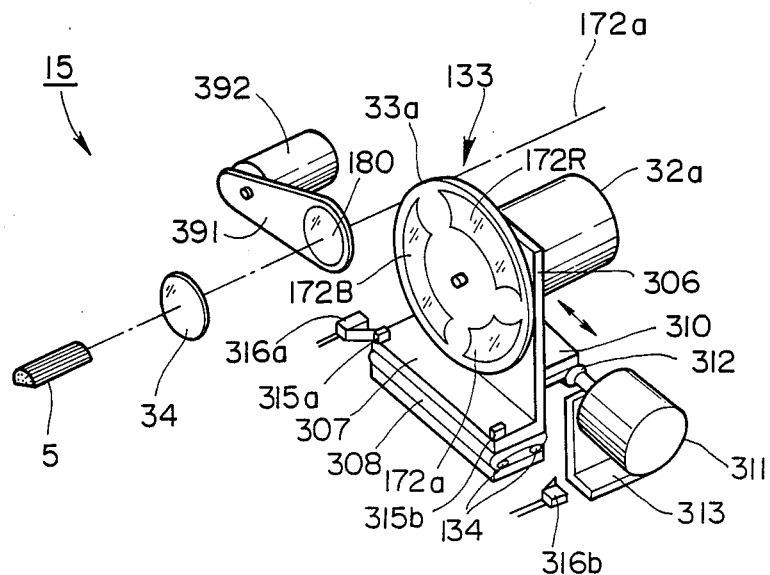
FIG. 36 is a perspective view showing the formation of a light source apparatus using a rotary solenoid relating to the ninth embodiment of the present invention.

FIG. 36 is a perspective view showing the formation of a light source apparatus relating to the ninth embodiment of the present invention.

In this embodiment, a rotary solenoid is provided in an example of the concrete formation of the light source apparatus in the second embodiment.

The above mentioned rotary filter 33a and the motor 32a rotating and driving it are moved and retreated from the above mentioned optical axis 172a by a mechanism such as is shown in FIG. 36. That is to say, the above mentioned monitor 32a is fitted to a plate-like fitting bracket 306 below which a horizontally bent flange part 307 is formed. Below this flange part 307, two rails 134 fixed to the housing side of the control apparatus are parallelly provided. In the bottom of the above mentioned flange part 307, a sliding part 308 in the form holding these rails from the right and left is formed and is fitted slidably to the above mentioned rails 134 so that the rotary filter part 133 consisting of the above mentioned rotary filter 33a, motor 32a and rotary position sensor, not illustrated, may be movable.

On the surface of the light source lamp side not illustrated of the above mentioned fitting bracket 306. A rack gear 310 is fitted along the moving direction of the above mentioned rotary filter part 133. A worm gear 312 rotated by the rotary motor 311 is fitted to this rack gear 310. The rotary motor 311 is fixed to the housing side of the control apparatus by a bracket 313. By normally and reversely rotating the above mentioned motor 311, the above mentioned rotary filter part 133 can be moved through the above mentioned worm gear 312 and rack gear 310.

The above mentioned motor 311 is controlled by the movement controlling circuit 135 shown, for example, in FIG. 12.

On the upper surface of both end parts in the moving direction of the flange part 308 of the above mentioned fitting bracket 306, flat prismatic switch pressing parts 315a and 315b are provided to project. Switching position detecting microswitches 316a and 316b are arranged in the positions pressed by the above mentioned switch pressing parts 315a and 315b at both ends of the moving range of the above mentioned rotary filter part 133. When these microswitches 316a and 316b are pressed by the above mentioned switch pressing parts 315a and 315b, it will be sensed that the above mentioned rotary filter part 133 has reached the end of the moving range, the rotation of the above mentioned motor 311 will be stopped and the moving range of the rotary filter part 133 will be regulated.

In the illustrated example, when the switch pressing part 315a presses the microswitch 316a, the color transmitting filters 172R, 172G and 172B of the rotary filter 33a will be interposed in the above mentioned optical axis 172a and the white light will pass through the above mentioned color transmitting filters 172R, 172G and 172B. When the switch pressing part 315b presses the microswitch 316b, the above mentioned rotary filter 33a will retreat from the above mentioned optical axis 172a. At this time, though the details of the formation are not illustrated, a rotary solenoid 392 having a rotary arm 391 fitted with the concave lens 180 pivoted to the rotary shaft is operatively connected. The concave lens 180 fitted to the proximal end of the rotary arm 391 of the above mentioned rotary solenoid 392 rotates to the optical axis 172a and is interposed.

Therefore, according to the ninth embodiment in the present invention, in case the rotary filter 33a is on the optical axis 172a, the concave lens 180 will be retreated by the rotary solenoid 392 and the light reduction when the illuminating light passes through the color transmitting filters 172R, 172G and 172B can be compensated by focusing the illuminating light on the end surface of the light guide 5 with the condenser lens 34. In case the rotary filter 33a is retreated from the optical axis 172a, the concave lens 180 is interposed in the optical axis 172a by the rotary solenoid and the illuminating light is defocused on the end surface of the light guide 5 and the fear of burning the end surface of the light guide 5 can be dissolved.

Figure 37:
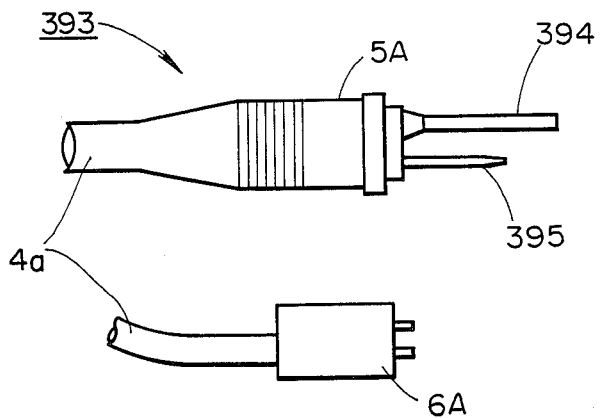
FIGS. 37 is 38 relate to the tenth embodiment of the present invention.

FIGS. 37 and 38 show the tenth embodiment of the present invention.

In FIG. 37, a connector part 393 of the frame sequential type electronic scope 2A is formed of a light source connector 5A fitted to the light source connector receptacle 11 provided on the front surface of the above mentioned control apparatus 1a, a signal connector 6A fitted to the signal connector receptacle 12 and universal cords 4a extended respectively from these light source connector 5A and signal connector 6A. The above mentioned light source connector 5A is provided with an illuminating system terminal part 394 through which a light guide 5 consisting of a fiber bundle provided to project formed of the end surface is inserted and an air and water feeding system terminal part 395.

Figure 38A:
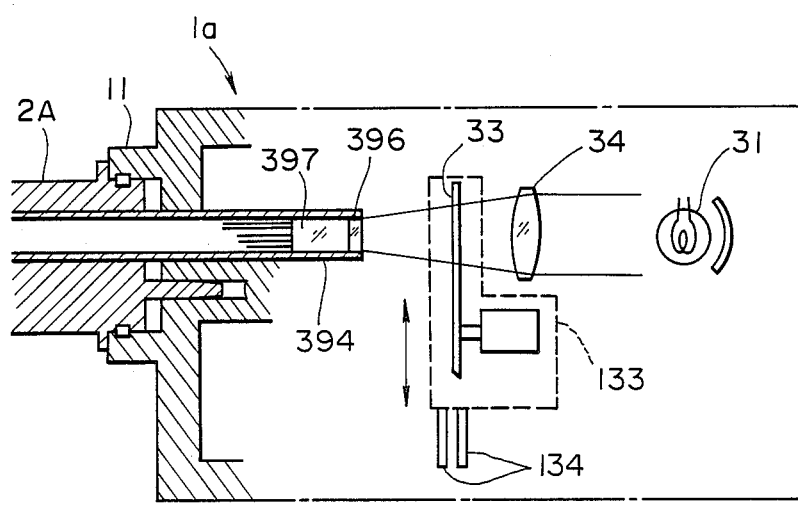
FIG. 38(a) is an explanatory view showing the state of an illuminating light when a light source connector of a frame sequential type electronic scope is fitted to a control apparatus.

Now, the above mentioned illuminating system terminal part 394, in FIG. 38(a), is made in an air-tight structure closed on the tip end surface with a cover glass 396 within which a rod lens 397 is provided and connected.

In FIG. 38(a), the light source connector 5A of the above mentioned frame sequential type electronic scope 2A is fitted to the light source connector receptacle 11 on the front surface of the control apparatus 1a and the illuminating light emitted from the light source lamp 31 is condensed by the condenser lens 34 and is focused on the front end surface of the above mentioned illuminating system terminal part 394 through the rotary filter 33.

Figure 38B:
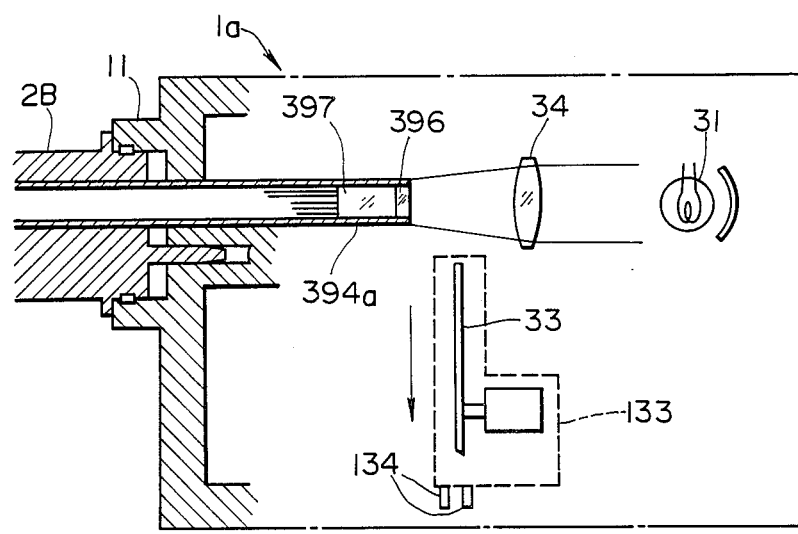
FIG. 38(b) is an explanatory view showing the state of an illuminating light when a light source connector of a fiber scope or color mosaic type electronic scope is fitted to a control apparatus.

In case the fiber scope 2E and color mosaic type electronic scope 2B requiring a white illumination is fitted, as shown in FIG. 38(b), as an illuminating system terminal part 394a fits deeper into the control apparatus 1a from the fitting part as compared with the above mentioned illuminating system terminal part 394, the illuminating light emitted from the light source lamp 31 will be defocused on the front end surface.

At this time, the rotary filter part 133 will retreat from the light path by a mechanism such as is shown, for example, in the ninth embodiment.

The retreat of the above mentioned rotary filter part 133 is to sense the fiber scope 2E and color mosaic type electronic scope 2B against the frame sequential type electronic scope 2A by a scope discriminating means within the control apparatus 1a though not illustrated. This sensing means may be, for example, as described above, to sense it with various electric resistances provided within the light source connector of the scope on the control apparatus 1a side at the time of connecting the scope.

In the case of the electronic scope, a sensing method by a signal from the video process circuit or by the connection of a cable with the video process circuit will do.

The position of the front end surface of the above mentioned illuminating system terminal part at the time of a white illumination may be a defocusing position and is not limited to the position in FIG. 38(b).

Further, the positioning of the front end surface of the above mentioned illuminating system terminal part 344a is not limited to the example in FIG. 38(b). Anything will do if the object is attained.

The effect of the tenth embodiment in the present invention is the same as of the eighth embodiment.

Figure 39:
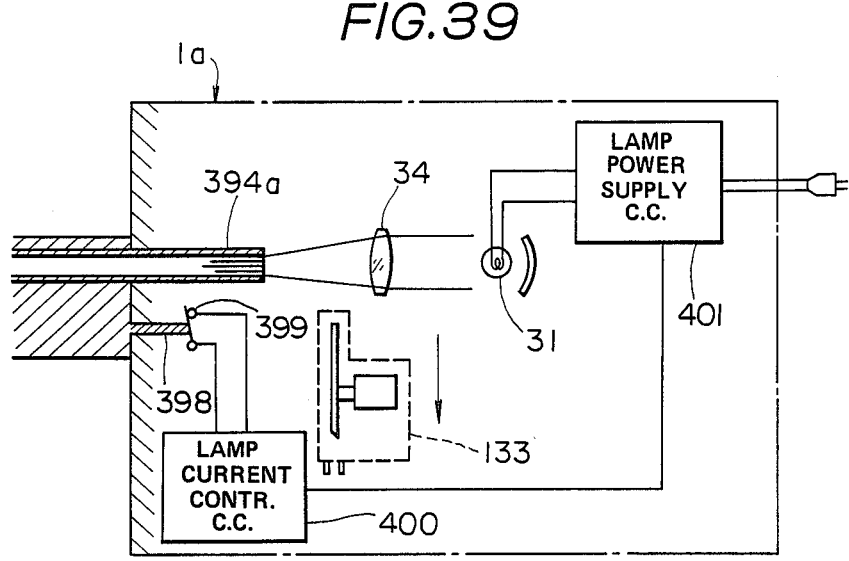
FIG. 39 relates to the eleventh embodiment of the present invention and is an explanatory view showing that the generated light amount of a light source lamp is controlled by a lamp current controlling circuit of the illuminating light when the light source connector of a fiber scope or color mosaic type electronic scope is fitted to the control apparatus.

FIG. 39 shows the eleventh embodiment of the present invention.

The front part of the light source connector 5E or 5B of the fiber scope 2E or mosaic type electronic scope 2B requiring a white illuminating light is provided with a pressing pin 390 to project so as to be sensed as distinguished from the frame sequential type electronic scope 2A. When the light source connector 5E or 5B of the fiber scope 2E or color mosaic type electronic scope 2A is fitted to the light source connector receptacle 11 on the front surface of the above mentioned control apparatus 1a, the above mentioned pressing pin 398 will press a switch 399 provided within the control apparatus 1a so as to be conductive. When the above mentioned switch 399 is pressed to be conductive, the lamp power source controlling circuit 400 will operate and the current fed to the light source lamp 31 from the lamp power source circuit 401 will be controlled to reduce the light amount of the above mentioned light source lamp 31.

At this time, the rotary filter part 133 will retreat by the same mechanism as, for example, in the ninth embodiment.

Therefore, though the white illuminating light from the above mentioned light source lamp 31 entering the tip surface of the illuminating system terminal part 394a provided to project on the light source connector 5E or 5B of the fiber scope 2E and color mosaic type electronic scope 2B is focused on the tip surface of the above mentioned illuminating system terminal part 394a, as the light amount is reduced by the above mentioned lamp current controlling circuit 401, the problem of burning the end surface of the above mentioned light guide 5 will be solved and an illuminating light of a proper light amount can be fed.

The scope kind discriminating method is as described above in the tenth embodiment. It may be sensed with various electric resistances provided within the light source connector and is not limited to only FIG. 39.

Figure 40:
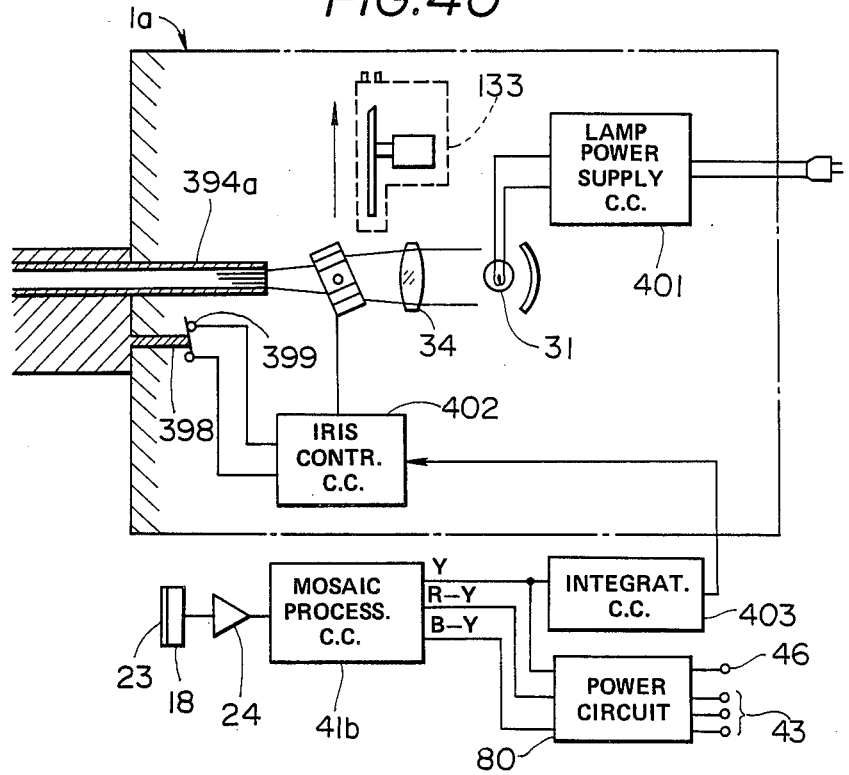
FIG. 40 relates to the twelfth embodiment of the present invention and is an explanatory view showing that the illuminating light when a color mosaic type electronic scope is fitted to the control apparatus is adjusted by a diaphragm controlling controlling circuit.

FIG. 40 relates to the twelfth embodiment of the present invention and is an explanatory view showing the case that the illuminating light is adjusted by a diaphragm controlling circuit when the color mosaic type electronic scope is fitted to the control apparatus.

In FIG. 40, when the color mosaic type electronic scope 2B is fitted to the control apparatus 1a, a light measuring signal when the luminance signal Y output from the color mosaic type process circuit 41b is obtained through an integrating circuit 403 and a discriminating signal when the scope kind is sensed by using the pressing pin 398 the same as in the eleventh embodiment are input into a diaphragm controlling circuit 402. The above mentioned diaphragm controlling circuit 402 is to control the diaphragm value of the white illuminating light emitted from the light source lamp 31 from the above mentioned light measuring signal and discriminating signal. This diaphragm value may control the illumination intensity of the tip surface of the above mentioned light guide 5 not to be above certain value, for example, at the time of a white illumination.

Here, the rotary filter part 133 may be made to retreat from the light path by using the same mechanism as, for example, in the ninth embodiment.

The effect of the twelfth embodiment is the same as of the eleventh embodiment.

The scope kind discriminating method is not limited to FIG. 40.

The thirteenth embodiment of the present invention shall be explained by using FIGS. 34 and 36.

In FIGS. 34 and 36, when, instead of the concave lens 180, meshes having a proper light intercepting effect are provided for the white light hole, the illumination light from the light source lamp 31 will be radiated as reduced on the entering end surface of the light guide 5 of the fiber scope 2E or color mosaic type electronic scope 2B.

The effect of the thirteenth embodiment is the same as of the eighth embodiment.

The fourteenth embodiment of the present invention shall be explained by using FIG. 35.

In FIG. 35, in the case of fitting the frame sequential type electronic scope 2A, when an illuminating light is radiated onto the light guide 5 with a light amount distribution of the curve B having a high condensing degree, a large illuminating light amount will be obtained with a small number of light guide fibers. Also, in case the fiber scope 2E and color mosaic type electronic scope 2B are fitted, when an illuminating light is radiated on the light guide 5 with the light amount distribution of the curve A, the maximum illumination intensity can be reduced.

The effect of the fourteenth embodiment is the same as of the eighth embodiment.

The transmitting filters are not limited to the R, G and B filters and include all of such transmitting filters for observation as infrared cut filters. For example, an observation by a visible light or infrared light can be made with an infrared cut filter.

The concave lens is used for defocusing on the entrance end surface of the light guide of the illuminating light when the fiber scope and color mosaic type electronic scope are used but a convex lens can be used.

Figure 41:
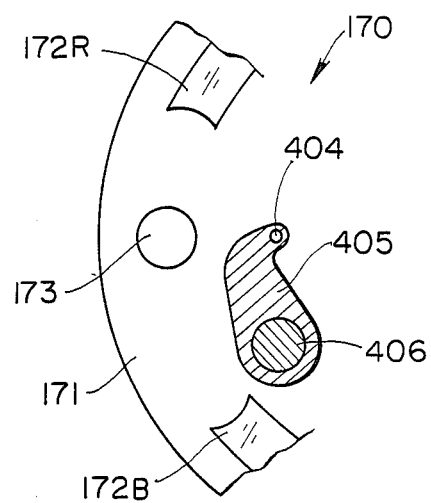
FIG. 41 relates to the thirteenth embodiment of the present invention and is an explanatory view showing the formation of a rotary filter.

FIG. 41 is an explanatory view showing the formation of a rotary filter showing the thirteenth embodiment. In this embodiment, a weight 406 is fitted to a light intercepting plate 405 fitted rotatably with a position on a segment connecting the white illuminating hole 173 and the center as a pivotal point 404 in the light intercepting part, for example, between R and B color transmitting filters 172R and 172B and the response to the rotating and stopping operations of the rotary filter 170 is improved as compared with the seventh embodiment.

The other formations are the same as of the seventh embodiment.

Figure 42:
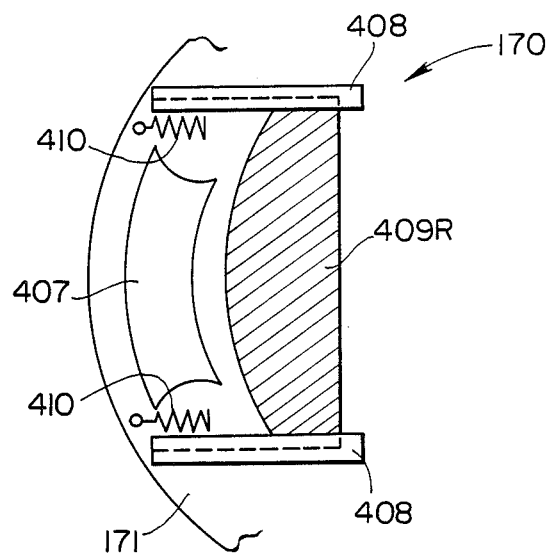
FIG. 42 relates to the fourteenth embodiment of the present invention and is an explanatory view showing the formation of a rotary filter.

FIG. 42 is an explanatory view showing the formation of a rotary filter showing the fourteenth embodiment. In this embodiment, two rails 408 are extended in the radial direction of the filter frame 171 on both sides in the rotating direction of a hole 407 provided on a filter frame 171. For example, an R color transmitting filter 409R of a size capable of covering the above mentioned hole 407 is slidably fitted in the radial direction of the filter frame 171. Springs 410 fixed to the filter frame 171 are fitted in the center direction on the hole 407 side of the above mentioned rails 408. When the filter frame 171 is rotated by the motor 32a, the above mentioned color transmitting filter 409R will be moved to the radial outer peripheral side of the filter frame 171 against the energizing force of the above mentioned springs 410 by the centrifugal force to cover the above mentioned hole 407. In the same manner, when G and B color transmitting filter 409G and 409R are provided in the peripheral direction of the filter frame 171, ordinary R, G and B frame sequential illumination can be made. On the other hand, when the above mentioned filter frame 171 is stopped, no centrifugal force will work, therefore the color transmitting filters 409R, 409G and 409B will be moved to the radial direction center side of the filter frame 171 by the above mentioned spring 410 and will retreat from the above mentioned hole 407 and the hole 407 will become a white light hole.

By such a formation, it is no more necessary to provide a hole exclusively for the white light.

In the above described respective embodiments, a correcting circuit means for correcting the temperature dependency of the light emitting characteristics of the light source lamp 31 or the like may be provided.

Also, a color-temperature converting filter in response to the characteristics of the fitted scope may be interposed in the light path of the illuminating light from the light source lamp 31 so that, in the case of using the electronic scope, in response to the prismatic characteristics of the used solid state imaging device, a light beam having the optimum energy distribution can be selected.

Different embodiments can be formed by combining parts of the above described respective embodiments and belong to the present invention.

The light source apparatus of present invention is not limited to be used as combined with the video processor as in the above described embodiments but may be singly used.

What is claimed is:

1. An endoscope light source apparatus to which an endoscope provided with a frame sequential type color imaging means, an endoscope provided with a color mosaic type color imaging means and an optical endoscope can be connected, said endoscope light source apparatus comprising:
   a frame sequential light outputting means for outputting an illuminating light to said frame sequential type color imaging means; and
   a white light outputting means for outputting an illuminating light to said color mosaic type color imaging means.

2. An endoscope light source apparatus according to claim 1 wherein said white light outputting means is a white light outputting light source provided separately from a light source forming said frame sequential light outputting means.

3. An endoscope light source apparatus according to claim 2 wherein said frame sequential light outputting means has three primary colors of red, green and blue transmitting filters driven by a driving motor, arranged between said light source and an object to be imaged and sequentially transmitted respective color lights of red, green and blue.

4. An endoscope light source apparatus according to claim 1 wherein said white light outputting means comprises a white light emitting light source, respective red, green and blue color lights sequentially transmitting filters arranged removably between said white light emitting light source and an object to be imaged and a moving means for moving said filters so that white light emitted from said white light emitting source may be radiated onto said object without passing through said filters.

5. An endoscope light source apparatus according to claim 4 wherein said filters form a rotary filter driven by a driving motor and having a position detecting means for detecting positions of said filters.

6. An endoscope light source apparatus according to claim 4 wherein said moving means is moved by meshing a worm gear with a rack gear.

7. An endoscope light source apparatus according to claim 4 wherein said moving means is moved by meshing a rack gear with a pinion.

8. An endoscope light source apparatus according to claim 4 wherein said moving means is provided with a filter and a driving motor driving said filter at one end of a fitting bracket and a rocking motor is connected to another end to rock said filter.

9. An endoscope light source apparatus according to claim 4 wherein said moving means is provided with a filter and a driving motor driving said filter slidably on rails.

10. An endoscope light source apparatus according to claim 4 wherein said moving means is controlled by a movement controlling means into which a discriminating signal discriminating endoscope type is input.

11. An endoscope light source apparatus according to claim 4 wherein said moving means is controlled in movement by an information signal representing that a position detecting means and a separately provided signal processing means for producing a video signal are electrically connected with each other.

12. An endoscope light source apparatus according to claim 4 wherein said white light outputting means has a light amount adjusting means, removably arranged between said white light emitting light source and object to be imaged, for adjusting an amount of white light emitted from the white light emitting light source.

13. An endoscope light source apparatus according to claim 1 wherein said white light outputting means comprises a light source emitting a white light, filters arranged between said light source and object to be imaged and sequentially transmitting respective color lights of red, green blue, and a moving means for moving said light source so that the white light emitted from said light source may be radiated onto said object without passing through said filter.

14. An endoscope light source apparatus according to claim 13 wherein said moving means is controlled by a movement controlling means into which a discriminating signal discriminating endoscope type is input.

15. An endoscope light source apparatus according to claim 1 wherein said white light outputting means comprises a light source emitting a white light, a filter frame arranged between said light source and object to be imaged and provided with filters sequentially transmitting three color lights including a white light and a rotation/stop controlling means for stopping said filter frame in a position of transmitting said white light.

16. An endoscope light source apparatus according to claim 1 wherein said white light outputting means comprises a light source emitting a white light, a filter frame arranged between said light source and object to be imaged and provided with filters sequentially transmitting respective color lights of red, green, blue, and a rotation/stop controlling means for stopping said filter frame in a position of transmitting said white light.

17. An endoscope light source apparatus according to claims 15 or 16 wherein said filters form a rotary filter driven by a driving motor and having a position detecting means for detecting a position of the rotary filter.

18. An endoscope light source apparatus according to claims 15 or 16 wherein said rotation/stop controlling means controls a driving motor by inputting discriminating signal discriminating endoscope type and a filter position signal output by a position detecting means.

19. An endoscope light source apparatus according to claim 18 wherein said rotation/stop controlling means controls said driving motor with an information signal representing that said position detecting means and a separately provided and video signal producing signal processing means are electrically connected with each other.

20. An endoscope light source apparatus according to claim 17 wherein said rotary filter has a light intercepting plate intercepting the white light with a centrifugal force in case said rotary filter is rotating.

21. An endoscope light source apparatus according to claim 16 wherein a transmitting part has an optical lens system which can regulate an amount of illuminating light entering an entrance end surface of a light guide transmitting the white light emitted from the light source to the object.

22. An endoscope light source apparatus according to claims 2, 4, 13, 15 or 16 wherein said white light outputting means has a light source emitting a white light and a power source feeding means for controlling an amount of light emitting from said light source with an information signal representing endoscope type.

23. An endoscope light source apparatus according to claims 2, 4, 13, 15 or 16 wherein said white light outputting means has a light source emitting a white light and a diaphragm controlling means for controlling an amount of illuminating light emitted from said light source with an information signal representing endoscope type.

24. An endoscope light source apparatus according to claim 2, 4, 13, 15 or 16, wherein said white light outputting means has an optical lens system which can adjust an entering light amount entering an entrance end surface when said entrance end surface of a light guide means transmitting the illuminating light emitted from the white light outputting light source to said object approaches or retreats from said white light outputting light source.

25. An endoscope light source apparatus connectable with an endoscope provided with a frame sequential type color imaging means and an optical endoscope, said endoscope light source apparatus comprising:
a frame sequential light outputting means for outputting an illuminating light to a frame sequential type color imaging means; and
a white color light outputting means for outputting a white color illuminating light.

26. An endoscope light source apparatus according to claim 25 further comprising a light output controlling means for controlling said frame sequential light outputting means and said white color light outputting means with a discriminating signal which can discriminate the type of endoscope.

27. An endoscope light source apparatus according to claim 25 or 26 wherein said frame sequential light outputting means is provided with a plurality of filters, transmitting color lights in specific wavelength regions for obtaining a video signal, and a motor rotating and driving said filters.

28. An endoscope light source apparatus according to claim 27 wherein said white color light outputting means is provided with transmitting parts provided in said filters and transmitting white color light and a rotation/stop controlling means which positions said transmitting parts on an optical axis of a light source and which can stop the filters so as to transmit the white color light.

29. An endoscope rotary filter provided between a light source an outputting part outward outputting a light generated from said light source within a light source apparatus connected with an endoscope, said endoscope rotary filter comprising:
filters sequentially separating light generated from said light source into color lights in specific wavelength regions for obtaining a video signal;
transmitting parts transmitting as a white color light the light generated from said light source; and
a filter frame provided in a peripheral direction with said filters and said transmitting parts.

30. An endoscope rotary filter according to claim 29, further comprising a light intercepting means intercepting said white color light passing through said transmitting parts.

31. An endoscope rotary filter according to claim 29 or 30 wherein said filter frame is further provided with a position detecting hole.

32. An endoscope light source apparatus connectable with an endoscope provided with a frame sequential type color imaging means and an endoscope provided with a color mosaic type color imaging means comprising:
a frame sequential light outputting means for outputting an illuminating light to said frame sequential type color imaging means; and
a white color light outputting means for outputting an illuminating light to said color mosaic type color imaging means.

33. An endoscope light source apparatus according to claim 32 wherein said white light outputting means is a white light outputting light source provided separately from a light source forming said frame sequential light outputting means.

34. An endoscope light source apparatus according to claim 32 wherein said white light outputting means comprises a white light emitting light source, respective red, green and blue color lights sequentially transmitting filters arranged removably between said white light emitting light source and an object to be imaged and a moving means for moving said filters so that white light emitted from said white light emitting light source may be radiated onto said object without passing through said filters.

35. An endoscope light source apparatus according to claim 32 wherein said white light outputting means comprises a light source emitting a white light, filters arranged between said light source and an object to be imaged and sequentially transmitting respective color light of red, green, blue, and a moving means for moving said light source so that the white light emitted from said light source may be radiated onto said object without passing through said filter.

36. An endoscope light source apparatus according to claim 32 wherein said white light outputting means comprises a light source emitting a white light, a filter frame arranged between said light source and an object to be imaged and provided with filters sequentially transmitting three color lights including a white light and a rotation/stop controlling means for stopping said filter fame in a position of transmitting said white light.

37. An endoscope light source apparatus according to claim 32 wherein said white light outputting means comprises a light source emitting a white light, a filter frame arranged between said light source and an object to be imaged and provided with filters sequentially transmitting respective color light of red, green, blue, and a rotation/stop controlling means for stopping said filter frame in a position of transmitting said white light.

* * * * *